United States Patent
Hercouet

(10) Patent No.: US 7,905,927 B2
(45) Date of Patent: Mar. 15, 2011

(54) METHOD FOR LIGHTENING AND/OR COLORING HUMAN KERATIN FIBERS USING A COMPOSITION COMPRISING AN AMINOTRIALKOXY SILANE OR AMINOTRIALKENYLOXY SILANE COMPOUND AND DEVICE

(75) Inventor: Leïla Hercouet, Neuilly Plaisance (FR)

(73) Assignee: L'Oreal, SA, Paris (FR)

( * ) Notice: Subject to any disclaimer, the term of this patent is extended or adjusted under 35 U.S.C. 154(b) by 0 days.

(21) Appl. No.: 12/770,097

(22) Filed: Apr. 29, 2010

(65) Prior Publication Data

US 2010/0303748 A1    Dec. 2, 2010

Related U.S. Application Data

(60) Provisional application No. 61/177,311, filed on May 12, 2009, provisional application No. 61/177,313, filed on May 12, 2009.

(30) Foreign Application Priority Data

Apr. 30, 2009  (FR) ...................................... 09 52935
Apr. 30, 2009  (FR) ...................................... 09 52936

(51) Int. Cl.
*A61Q 5/10* (2006.01)
*A61K 8/89* (2006.01)

(52) U.S. Cl. ............. 8/405; 8/406; 8/410; 8/411; 8/431; 8/435; 8/501; 8/521; 8/581; 8/582; 8/632; 132/202; 132/208; 424/70.12

(58) Field of Classification Search ............. 8/405, 406, 8/410, 411, 431, 435, 501, 521, 581, 582, 8/632; 132/202, 208; 424/70.12
See application file for complete search history.

(56) References Cited

U.S. PATENT DOCUMENTS

2003/0150066 A1    8/2003  Richard
2006/0110351 A1*   5/2006  Koehler et al. ............ 424/70.12

FOREIGN PATENT DOCUMENTS

EP    1 298 135  A1    4/2003

OTHER PUBLICATIONS

STIC Search Report dated Sep. 30, 2010.*
French Search Report for FR 0952935, dated Jan. 12, 2010.
French Search Report for FR 0952936, dated Jan. 15, 2010.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure provides a method of lightening and/or coloring human keratin fibers comprising applying to the keratin fibers * at least one first composition comprising at least one fat, at least one nonionic surfactant, at least one specific aminotrialkoxy silane or aminotrialkenyloxy silane compound, and applying * at least one second composition comprising at least one oxidizing agent. It also provides a multiple-compartment device in which at least one compartment comprises the above-mentioned at least one first composition and at least one other compartment comprises the at least one oxidizing composition.

22 Claims, No Drawings

METHOD FOR LIGHTENING AND/OR COLORING HUMAN KERATIN FIBERS USING A COMPOSITION COMPRISING AN AMINOTRIALKOXY SILANE OR AMINOTRIALKENYLOXY SILANE COMPOUND AND DEVICE

This application claims benefit of U.S. Provisional Application Nos. 61/177,311 and 61/177,313, filed May 12, 2009. This application also claims benefit of priority under 35 U.S.C. §119 to French patent application Nos. 0952935 and 0952936, filed Apr. 30, 2009.

The present disclosure relates to a method of lightening and/or coloring human keratin fibers that employs, at least one composition comprising at least one silane chosen from aminotrialkoxy silane and aminotrialkenyloxy silane compounds and at least one oxidizing composition.

The present disclosure also relates to a multiple-compartment device or kit in which at least one compartment comprises the at least one composition comprising at least one silane and at least one other compartment comprises the at least one oxidizing composition.

The techniques for coloring human keratin fibers, such as the hair, include permanent or oxidation coloring. This means of coloring may employ at least one oxidation dye precursor, for example at least one oxidation base may be used in combination with at least one coupler.

Oxidation bases are typically selected from ortho- or para-phenylenediamines, ortho- or para-aminophenols, and heterocyclic compounds. These oxidation bases are colorless or weakly colored compounds which, in combination with oxidizing products, provide access to colored species by a process of oxidative condensation.

The shades obtained with these oxidation bases may often be varied by combining them with at least one coupler, the latter being selected, for example, from aromatic meta-diamines, meta-aminophenols, meta-diphenols, and certain heterocyclic compounds, such as indole compounds.

The variety of molecules employed as oxidation bases and couplers allows a rich palette of colors to be obtained.

The coloring method involves contacting the oxidation dye precursor or precursors with an oxidizing agent, which is frequently hydrogen peroxide, under alkaline conditions. One of the common difficulties may lie in the fact that the most commonly used alkaline agent is aqueous ammonia, whose function is to adjust the pH of the composition to an alkaline pH in order to allow the breakdown of the oxidizing agent. Hence the oxygen formed causes condensation of the oxidation dye precursors and a lightening of the fiber by virtue of the breakdown of the melanin present. The alkalifying agent also has another role, namely that of swelling the keratin fiber in order to promote the penetration of the oxidizing agent and the dyes to the interior of the fiber.

This alkalifying agent is typically highly volatile, and this causes unpleasantness to the user on account of the strong and fairly unpleasant odor of the ammonia which is given off during the procedure.

Moreover, the amount of ammonia given off can require the use of levels which are greater than those necessary, in order to compensate this loss. This is not without consequence for the user, who not only remains discomforted by the odor but may also be confronted with greater risks of intolerance, such as, for example, irritation of the scalp (stinging sensations).

Replacing all or some of the aqueous ammonia by at least one alkalifying agent may not result in compositions which are as effective as those based on aqueous ammonia, because these alkalifying agents may not provide sufficient lightening of the pigmented fibers in the presence of the oxidizing agent.

Another coloring technique employed is that of direct or semi-permanent coloring. This procedure involves applying direct dyes to the keratin fibers, said dyes being colored with coloring molecules which have an affinity for the fibers, and then allowing the molecules to penetrate by diffusion to the interior of the fiber, and then rinsing the fibers.

The direct dyes generally employed are selected from nitrobenzene, anthraquinonoid, nitropyridine, azo, methine, azomethine, xanthene, acridine, azine or triarylmethane direct dyes.

This coloring technique does not require the use of an oxidizing agent unless the desire is to lighten the fiber at the same time as coloring it. In the latter case, the procedure is as for oxidation dyeing, in other words contacting the keratin fibers with the dyeing composition in the presence of an oxidizing agent, such as hydrogen peroxide, under alkaline conditions, generally in the presence of aqueous ammonia. The user, consequently, may then be confronted once again with the same difficulties as those set out before for oxidation dyeing.

Further to the coloring procedures, it is likewise common to employ lightening procedures in which the keratin fibers are contacted with an oxidizing composition under alkaline conditions. These procedures only involve breaking down the melanin in the fibers, to a greater or lesser extent depending on the oxidizing agent selected. Thus a peroxygenated salt can lead, generally speaking, to more pronounced lightening than when using hydrogen peroxide alone under alkaline conditions. Irrespective of the oxidizing agent employed, however, the lightening procedures may require the use of hydrogen peroxide under alkaline conditions, such as in the presence of aqueous ammonia, to form or accelerate the formation of oxygen. Consequently, once again, the same difficulties can be encountered as those with the coloring procedures employed in the presence of an oxidizing agent and aqueous ammonia.

One aspect of the present disclosure is therefore to provide methods of coloring and/or lightening human keratin fibers that are intended for use in the presence of an oxidizing agent but which do not exhibit at least one of the disadvantages as the methods using the existing compositions owing to the presence of large amounts of aqueous ammonia, while remaining at least equally effective, from the standpoints both of lightening and of coloring, and which display high performance in terms of chromaticity and homogeneity.

It has also been noted that the method according to the disclosure can endow the hair thus treated with a soft and smooth feel, even when it is applied to hair which has been sensitized beforehand by chemical treatment.

Accordingly, disclosed here in is a method of coloring and/or lightening human keratin fibers, comprising applying to the fibers:

at least one first composition comprising at least one fat, at least one nonionic surfactant, and at least one compound of formula (I):

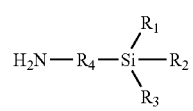

in which:
$R_1$, $R_2$ and $R_3$, which are identical or different, denote:
a linear or branched $C_1$-$C_{20}$ alkoxy radical in which the alkyl moiety is optionally interrupted by at least one oxygen atom, such as a linear or branched $C_1$-$C_{20}$, for example $C_1$-$C_4$ alkoxy radical,
a linear or branched $C_2$-$C_{20}$, for example $C_2$-$C_4$, alkenyloxy radical, $R_4$ is a divalent radical of structure:

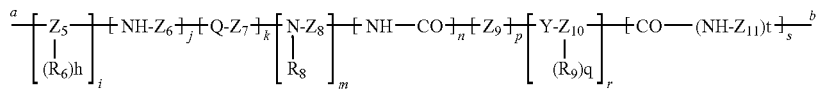

in which:
- $R_6$, identical or different at each occurrence, denotes a linear or branched $C_1$-$C_4$ alkyl radical, such as methyl or ethyl, which is optionally substituted by at least one entity chosen from hydroxyl groups, $NH_2$ radicals, hydroxyl radicals, cyano radicals, $Z_{12}NH_2$ radicals, $Z_{13}NH\ Z_{14}NH_2$ radicals, and linear or branched $C_2$-$C_{10}$, for example $C_2$-$C_4$, alkenyl radicals, with $Z_{12}$, $Z_{13}$, and $Z_{14}$ denoting, independently of one another, a $C_1$-$C_{20}$, such as $C_1$-$C_{10}$ or $C_1$-$C_4$ linear alkylene radical.
- $R_8$ denotes a linear or branched $C_1$-$C_4$ alkyl radical, for example methyl or ethyl, which is optionally substituted by at least one group chosen from hydroxyl and carboxyl groups, a linear or branched $C_2$-$C_{10}$, such as $C_2$-$C_4$, alkenyl radicals, $Z_{15}NH_2$ radicals, $Z_{16}R_8'$ radicals and $Z_{17}Si\ OSi(R_a)_2(R_b)$ radicals, where
- $R_a$ denotes a linear or branched $C_1$-$C_4$ alkoxy radical, such as methoxy or ethoxy
- $R_b$ denotes a linear or branched $C_1$-$C_4$ alkyl radical, such as methyl or ethyl
- $Z_{15}$, $Z_{16}$, and $Z_{17}$ denote, independently of one another, a $C_1$-$C_{20}$, for example $C_1$-$C_{10}$, such as $C_1$-$C_4$ linear alkylene radical
- $R_8'$ denotes a $C_6$-$C_{30}$ aryl radical, such as phenyl
- $R_9$ denotes a linear or branched $C_1$-$C_4$ alkyl radical
- $Z_5$, $Z_6$, $Z_7$, $Z_8$, $Z_9$, $Z_{10}$, and $Z_{11}$ denote, independently of one another, a $C_1$-$C_{20}$ linear alkylene radical
- Q denotes a ring containing six members which is saturated or unsaturated and optionally comprises at least one heteroatom
- Y, identical or different at each occurrence, represents an entity chosen from an oxygen atom, a sulphur atom and an NH group
- h is 0, 1, 2, 3, 4, or 5
- i is 0 or 1
- j is 0, 1, 2, or 3
- k is 0 or 1
- m is 0 or 1
- n is 0 or 1
- p is 0 or 1
- q is 0 or 1
- r is 0, 1, 2, or 3
- s is 0 or 1
- t is 1 or 2
- at least one of the coefficients chosen from h, i, j, k, m, n, p, q, r, s, and t is non-zero, such as at least one of the coefficients i, j, k, m, n, p, r, and s being non-zero;
- a represents the bond to the silicon atom,
- b represents the bond to the nitrogen atom of the amino group; and
- at least one second composition comprising at least one oxidizing agent.

The disclosure further provides a multiple-compartment kit comprising at least one first compartment containing at least one first composition as described above, and at least one second compartment containing at least one oxidizing composition.

Other features and benefits of the disclosure will emerge more clearly from a reading of the description and examples which follow.

In the text below, unless indicated otherwise, the end points of a range of values are included in that range.

The human keratin fibers treated by the method according to the disclosure include the hair.

As indicated above, the at least one first composition employed in the method according to the disclosure comprises at least one compound of formula (I).

In the formula (I), $R_1$ and $R_2$ can be identical.

According to at least one embodiment, the compound of formula (I) contains only one silicon atom.

Non-limiting examples of compounds of formula (I) that are suitable for the implementation according to the disclosure include the following compounds:

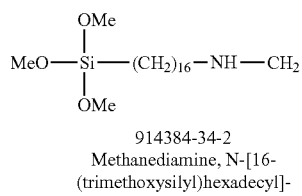

914384-34-2
Methanediamine, N-[16-(trimethoxysilyl)hexadecyl]-

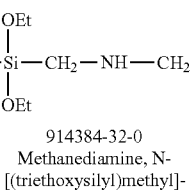

914384-32-0
Methanediamine, N-[(triethoxysilyl)methyl]-

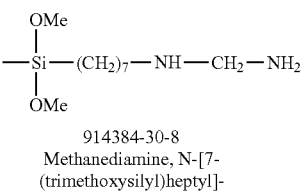

914384-30-8
Methanediamine, N-[7-(trimethoxysilyl)heptyl]-

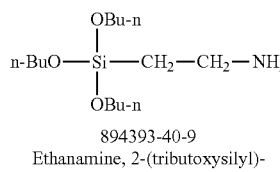

894393-40-9
Ethanamine, 2-(tributoxysilyl)-

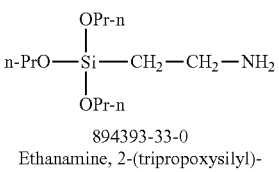

894393-33-0
Ethanamine, 2-(tripropoxysilyl)-

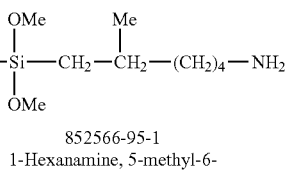

852566-95-1
1-Hexanamine, 5-methyl-6-(trimethoxysilyl)-

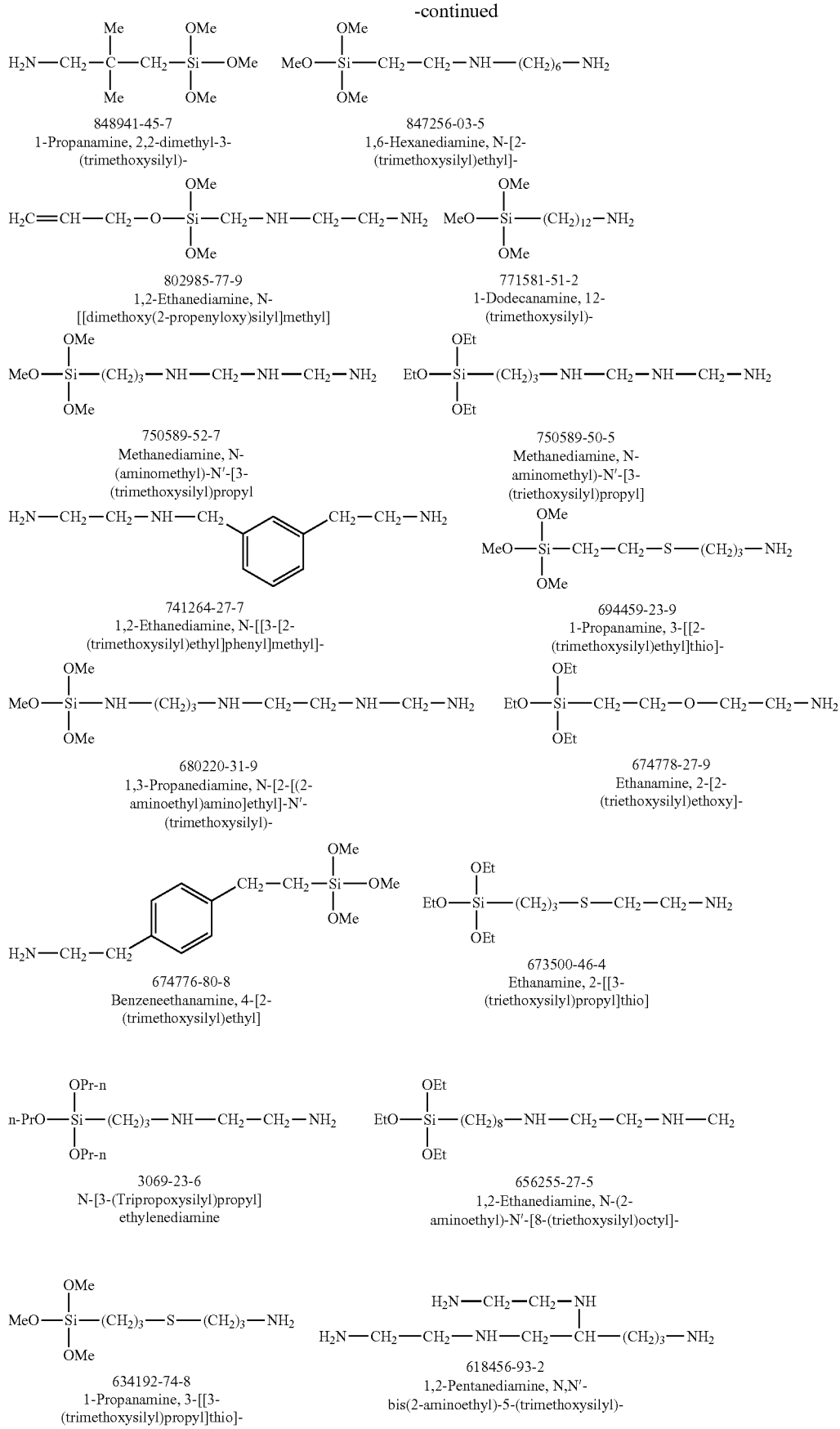

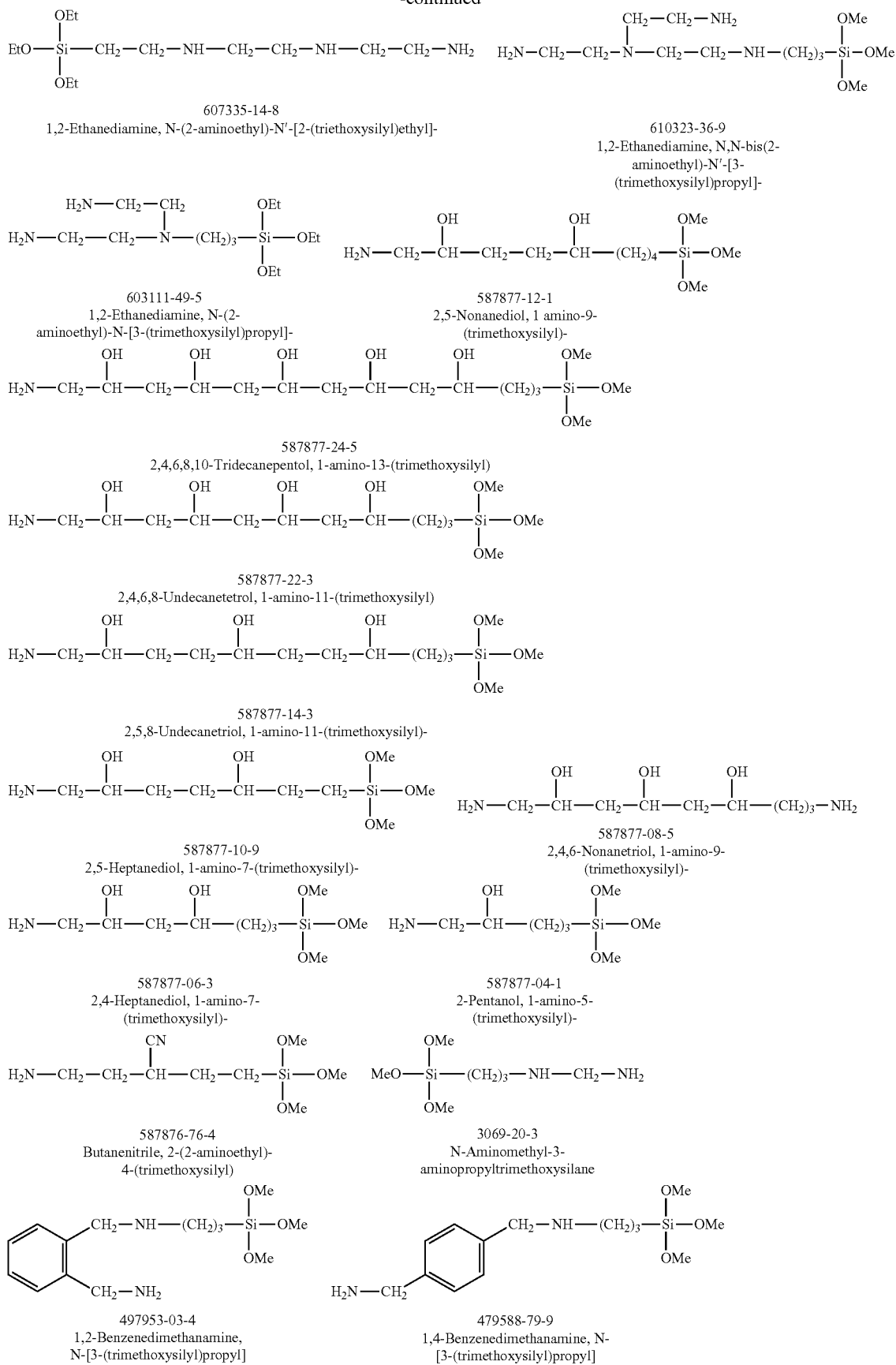

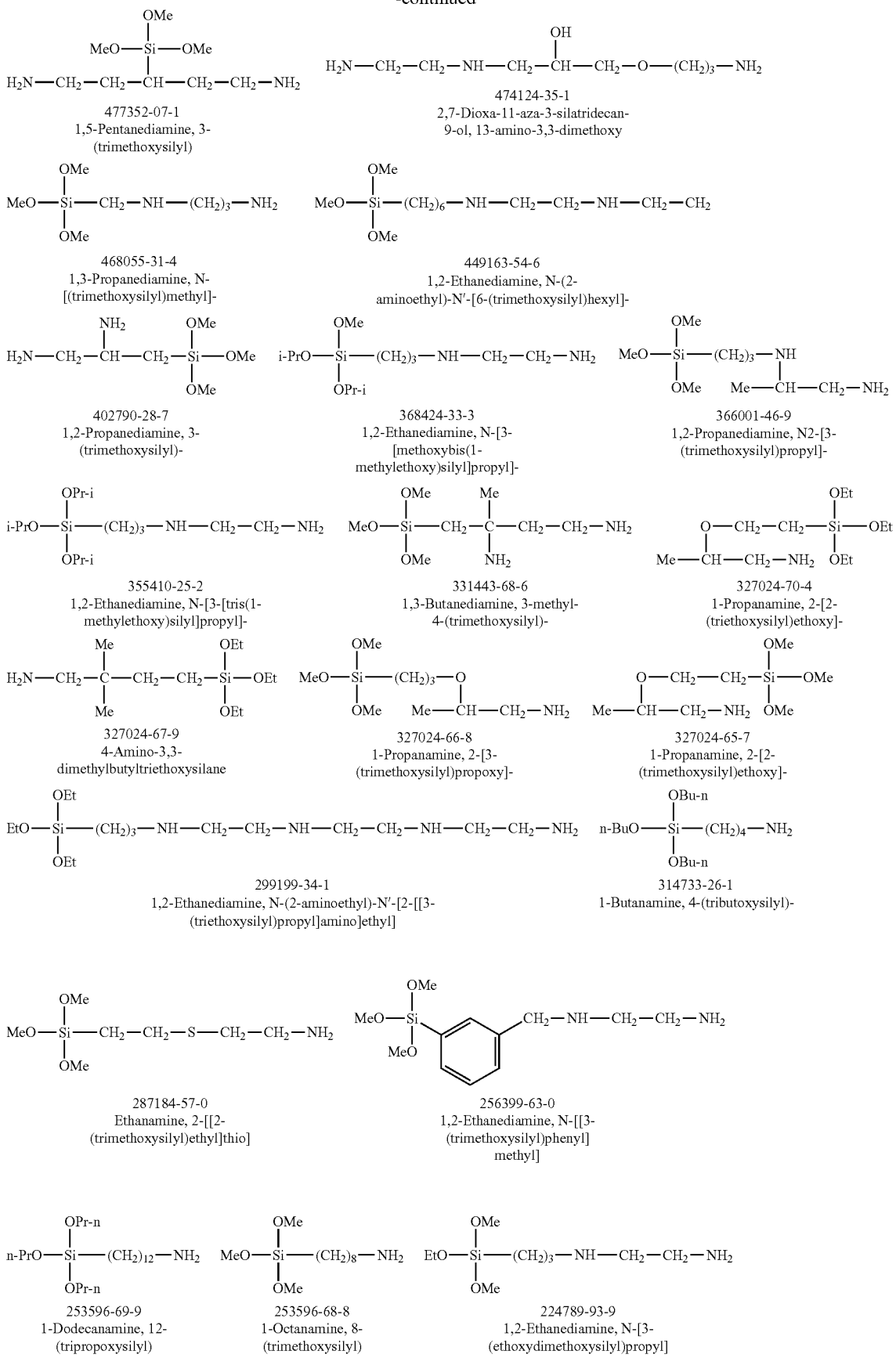

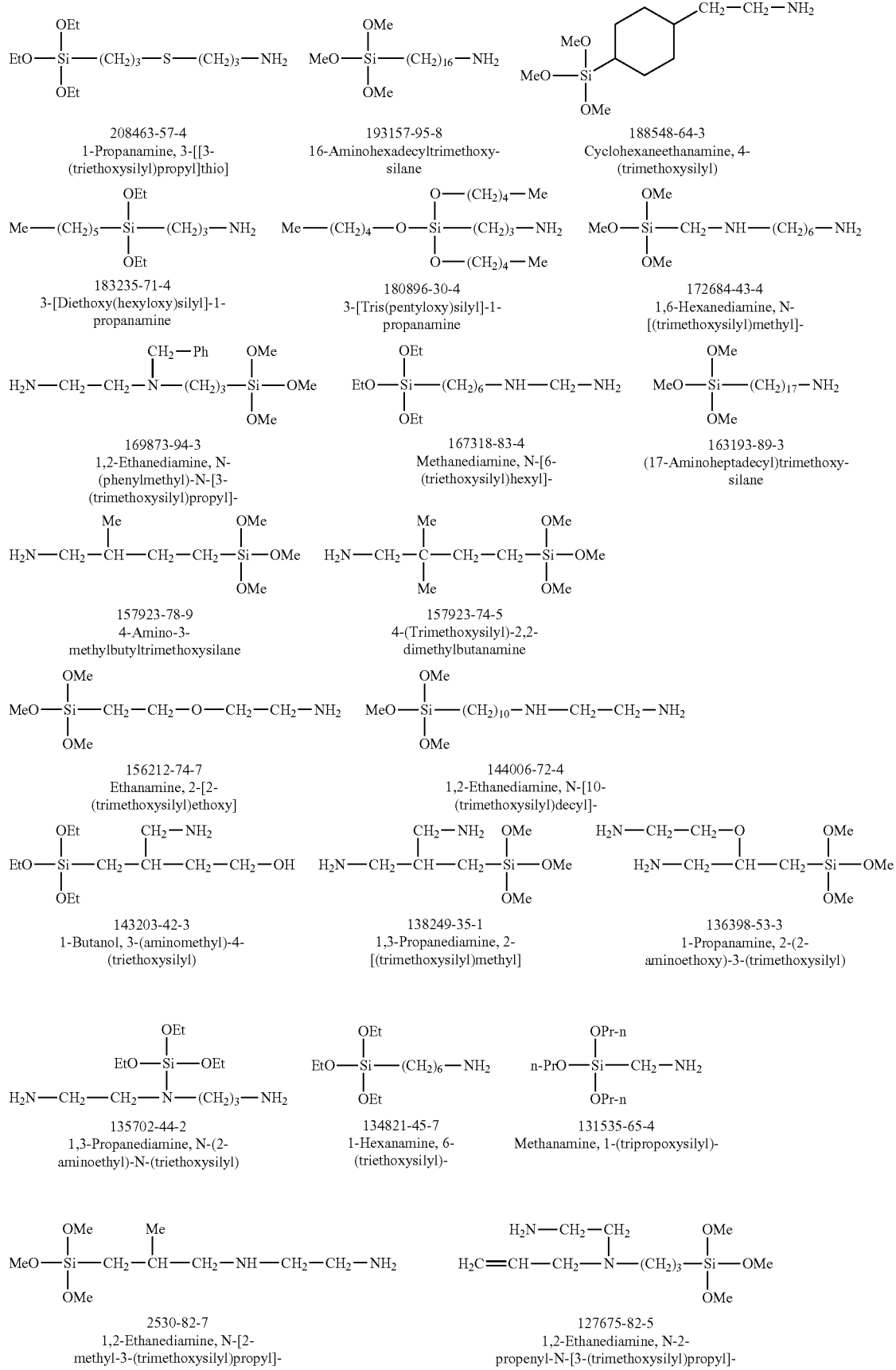

-continued

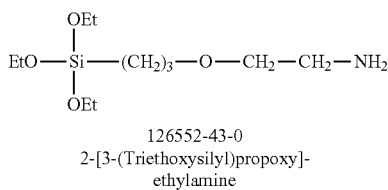
126552-43-0
2-[3-(Triethoxysilyl)propoxy]-ethylamine

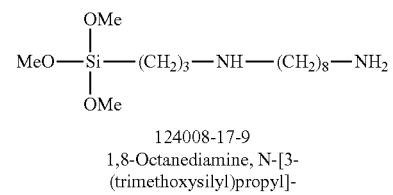
124008-17-9
1,8-Octanediamine, N-[3-(trimethoxysilyl)propyl]-

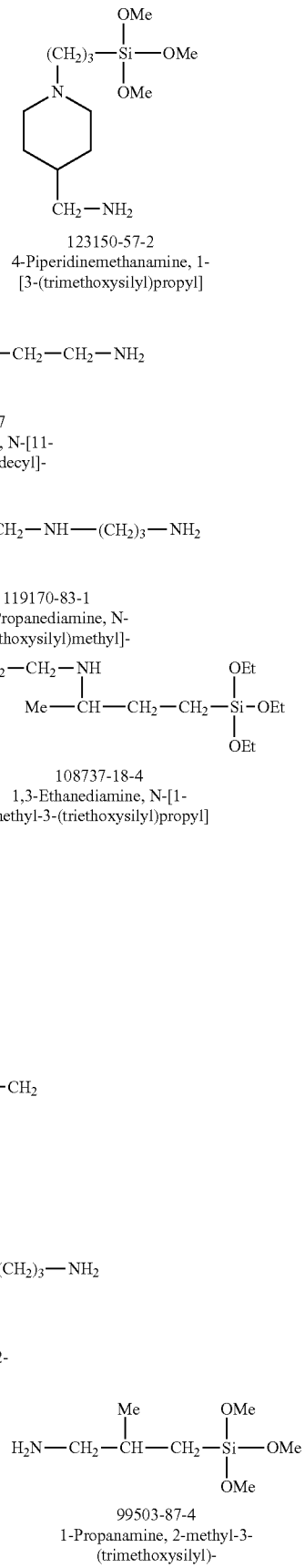
123150-57-2
4-Piperidinemethanamine, 1-[3-(trimethoxysilyl)propyl]

121487-64-7
1,3-Propanediamine, N-[2-[[3-(trimethoxysilyl)propyl]amino]ethyl]-

121772-92-7
1,2-Ethanediamine, N-[11-(trimethylsilyl)undecyl]-

120615-58-9
Ethanamine, 2-[[2-(triethoxysilyl)ethyl]thio]-

120183-15-5
(10-Aminodecyl)trimethoxysilane 119170-83-1
1,3-Propanediamine, N-[(triethoxysilyl)methyl]-

118746-32-0
1,3-Propanediamine, N-(2-aminoethyl)-N'-[3-(trmiethoxysilyl)propyl]

116821-45-5
11-(Aminoundecyl)triethoxysilane 108737-18-4
1,3-Ethanediamine, N-[1-methyl-3-(triethoxysilyl)propyl]

106894-51-3
1,2-Ethanediamine, N-(1-methylethyl)-N-[4-(triethoxysilyl)butyl]

106890-59-9
1-Butanamine, 3-methyl-4-(trimethoxysilyl)

104472-59-5
1,2-Ethanediamine, N-methyl-N-[3-(trimethoxysilyl)propyl]-

104261-39-4
Urea, N-(2-aminoethyl)-N'-[3-(triethoxysilyl)propyl]

104261-38-3
Urea, N-(2-aminoethyl)-N'-[3-(trimethoxysilyl)propyl]

104230-83-3
1,3-Propanediamine, N-[2-(triethoxysilyl)ethyl]-

103526-27-8
N,N-Di(2-aminoethyl)-3-aminopropyltrimethoxysilane 99740-25-7
1,3-Propanediamine, N-[3-(triethoxysilyl)propyl]-

99503-87-4
1-Propanamine, 2-methyl-3-(trimethoxysilyl)-

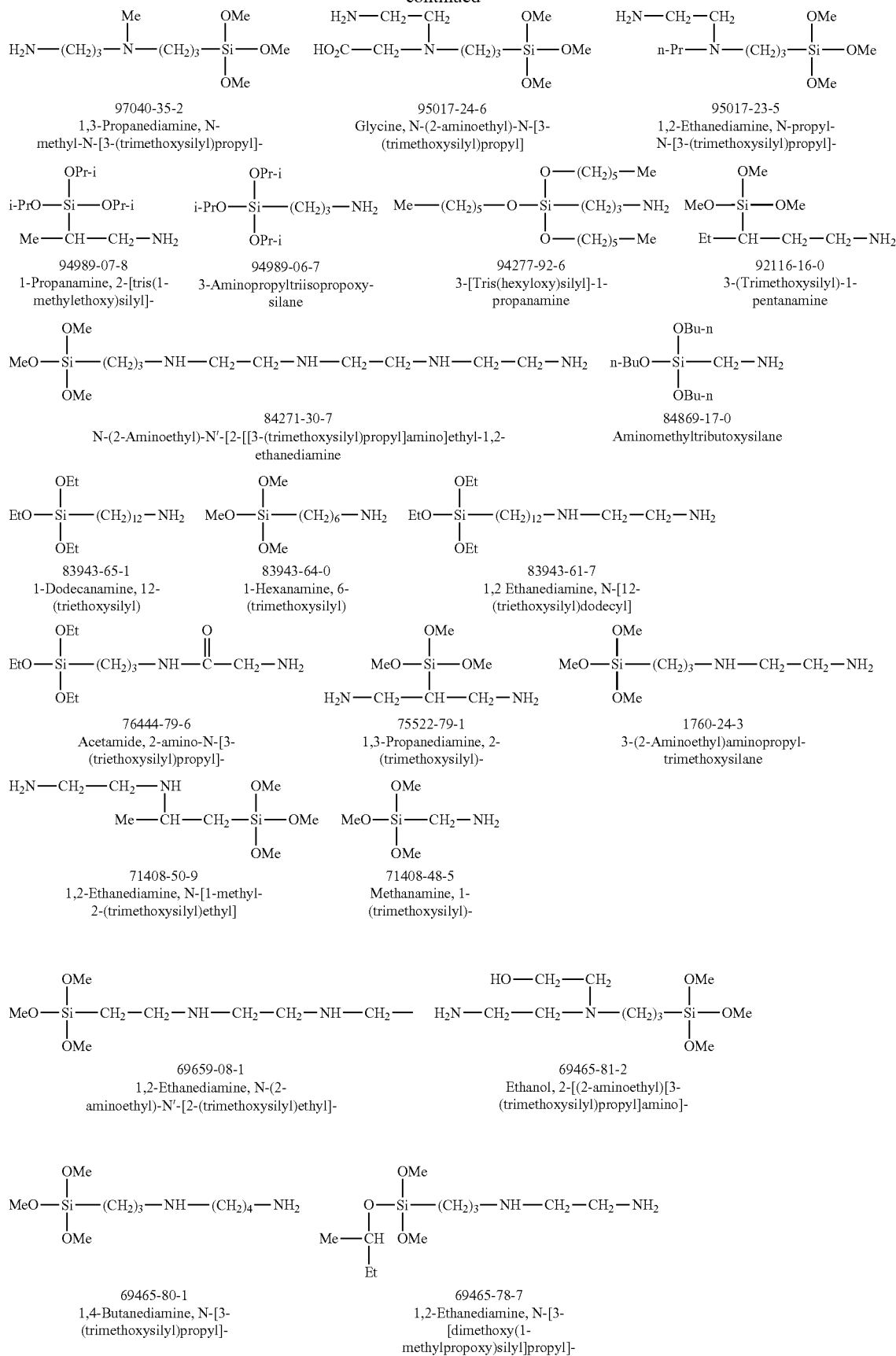

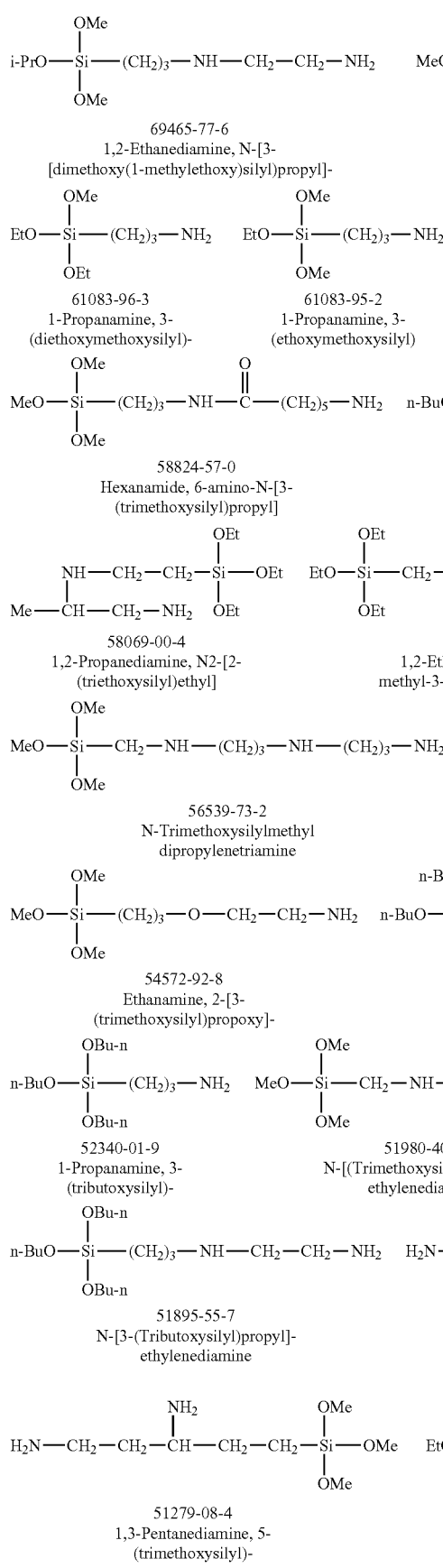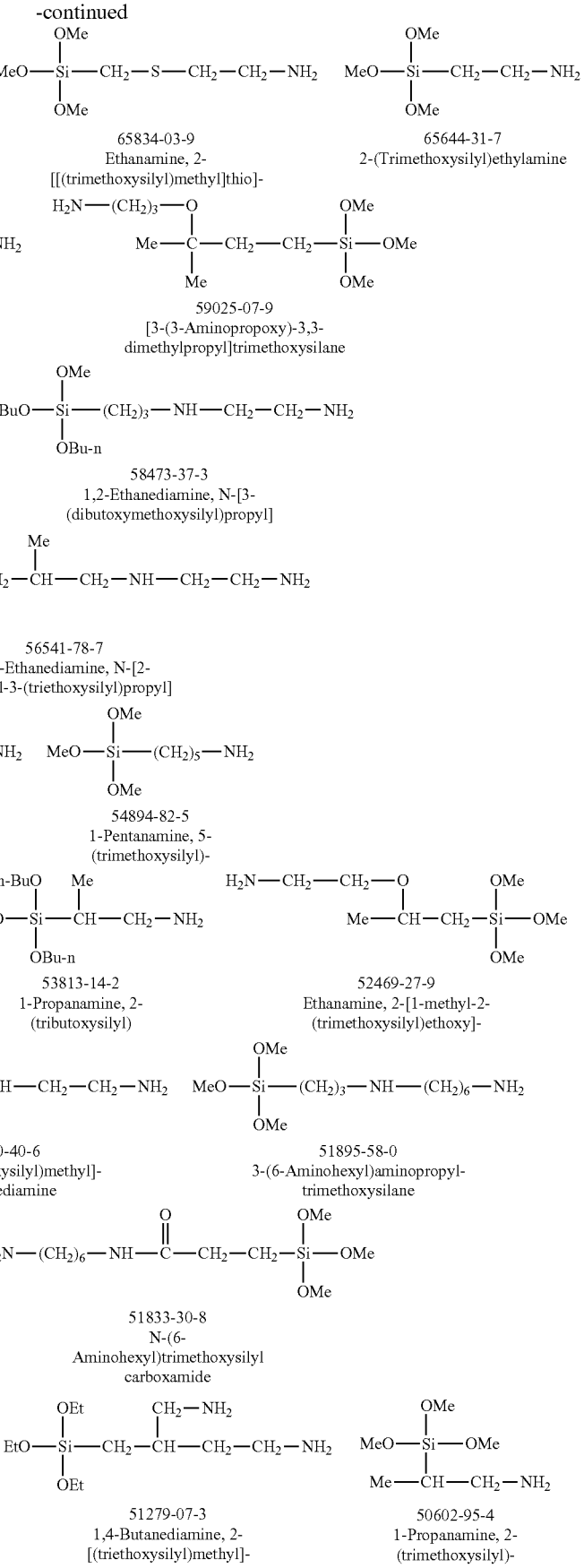

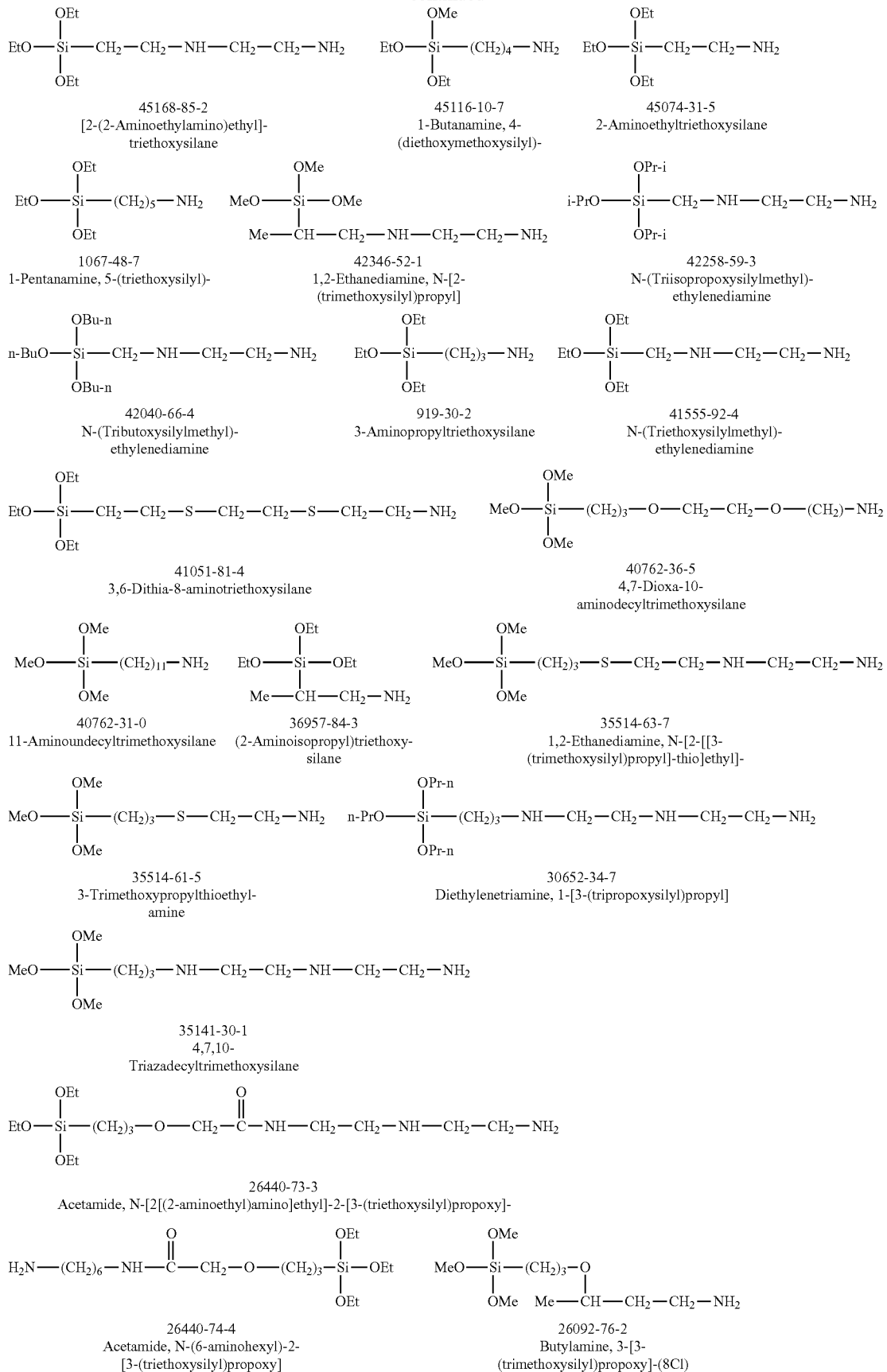

-continued

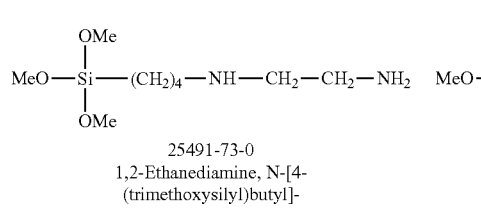

25491-73-0
1,2-Ethanediamine, N-[4-(trimethoxysilyl)butyl]-

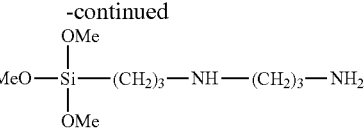

25147-91-5
3-[(3-Aminopropyl)amino]propyl-trimethoxysilane

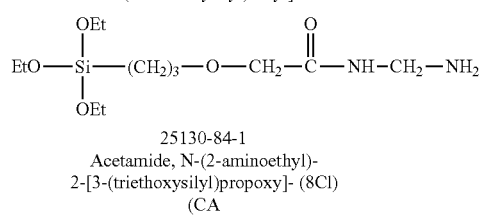

25130-84-1
Acetamide, N-(2-aminoethyl)-2-[3-(triethoxysilyl)propoxy]- (8Cl) (CA

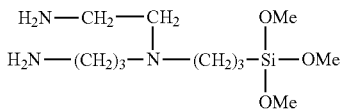

24763-39-1
1,3-Propanediamine, N-(2-aminoethyl)-N-[3-(trimethoxysilyl)propyl]

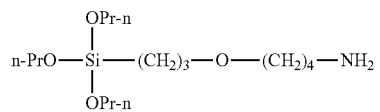

23386-49-4
Butylamine, 4-[3-(tripropoxysilyl)propoxy]

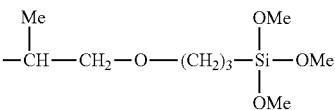

23386-47-2
3-(2-Methyl-3-aminopropoxy)-propyltrimethoxysilane

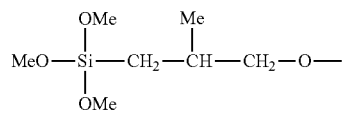

23386-46-1
Propylamine, 3-[2-methyl-3-(trimethoxysilyl)propoxy]

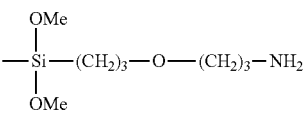

23386-45-0
3-[3-(Trimethoxysilyl)propoxy]-propylamine

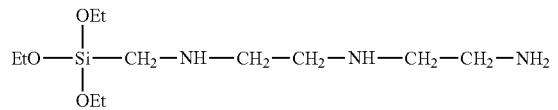

23021-89-8
1,2-Ethanediamine, N-(2-aminoethyl)-N'-[(triethoxysilyl)methyl]-

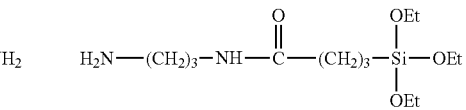

18551-50-3
Butyramide, N-(3-aminopropyl)-4-(triethoxysilyl)

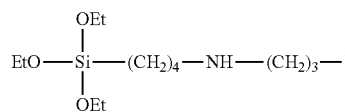

18418-52-5
1,3-Propanediamine, N-[4-(triethoxysilyl)butyl]

18306-83-7
Aminomethyltriethoxysilane

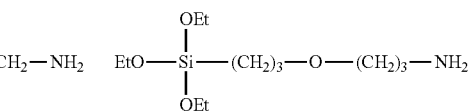

18082-90-1
(3-Aminopropoxy)propyl triethoxysilane

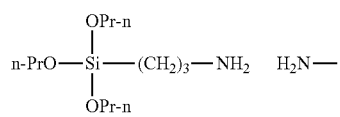

18082-68-3
1-Propanamine, 3-(tripropoxysilyl)

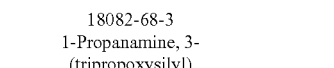

17961-40-9
1-Propanamine, 2-methyl-3-(triethoxysilyl)-

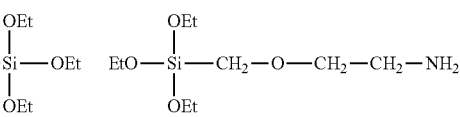

17886-99-6
2-[(Triethoxysilyl)methoxy]-ethylamine

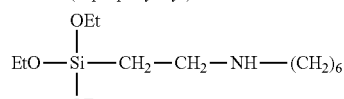

17576-02-2
1,6-Hexanediamine, N-[2-(triethoxysilyl)ethyl]

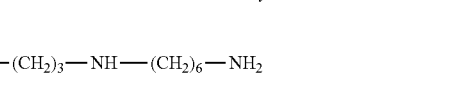

15484-16-9
1,6-Hexanediamine, N-[3-(triethoxysilyl)propyl]

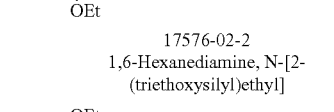

15129-36-9
N-[(Triethoxysilyl)methyl]-1,6-hexanediamine

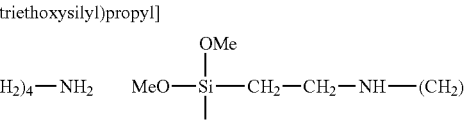

15005-59-1
(4-Aminobutyl)trimethoxysilane

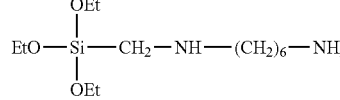

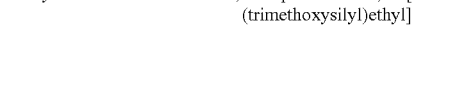

14513-31-6
1,3-Propanediamine, N-[2-(trimethoxysilyl)ethyl]

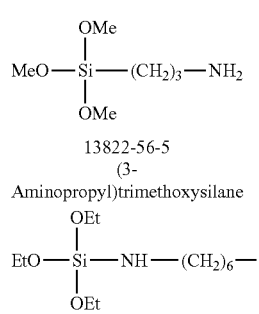
13822-56-5
(3-Aminopropyl)trimethoxysilane

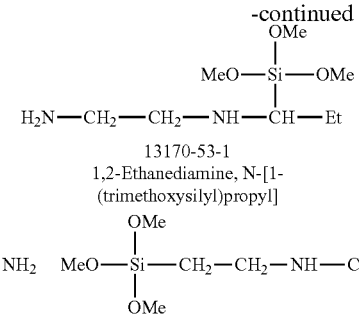
13170-53-1
1,2-Ethanediamine, N-[1-(trimethoxysilyl)propyl]

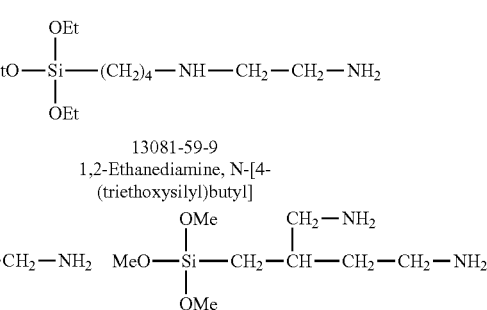
13081-59-9
1,2-Ethanediamine, N-[4-(triethoxysilyl)butyl]

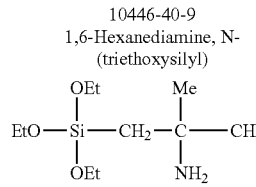
10446-40-9
1,6-Hexanediamine, N-(triethoxysilyl)

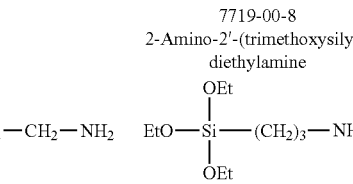
7719-00-8
2-Amino-2'-(trimethoxysilyl)-diethylamine 6037-49-6
1,4-Butanediamine, 2-[(trimethoxysilyl)methyl]

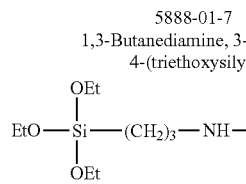
5888-01-7
1,3-Butanediamine, 3-methyl-4-(triethoxysilyl)

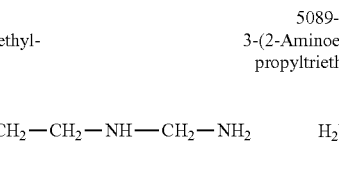
5089-72-5
3-(2-Aminoethylamine)-propyltriethoxysilane

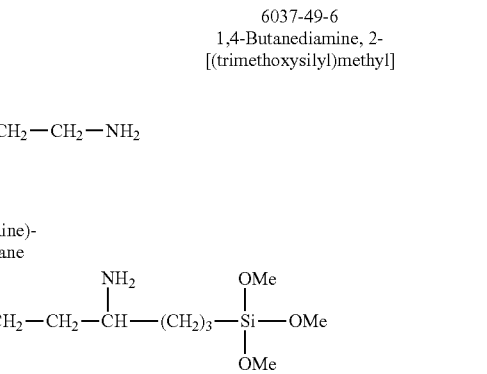

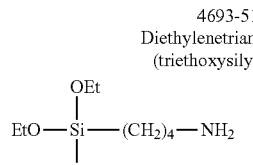
4693-51-0
Diethylenetriamine, 1-[3-(triethoxysilyl)propyl]

4543-14-0
1,3-Hexanediamine, 6-(trimethoxysilyl)

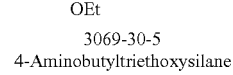
3069-30-5
4-Aminobutyltriethoxysilane

In at least one embodiment, $R_1$ and $R_2$ are identical as used in formula (I). In at least one embodiment, $R_1$, $R_2$, and $R_3$ are identical.

In accordance with this embodiment, the coefficients k, n, and s denote 0.

According to at least one embodiment, the compound of formula (I) comprises only one silicon atom.

According to at least one embodiment of the disclosure, the compounds of formula (I) contain only one silicon atom bearing three $C_1$-$C_4$ alkoxy groups.

According to this variant, $R_1$, $R_2$, and $R_3$ may be identical.

In accordance with at least one embodiment of this same variant, the coefficients k, n, and s denote 0; and p is 1.

In accordance with at least one embodiment, the compounds of formula (I) corresponding to the criteria of the variant detailed before are such that, in addition, the coefficients r, j and, m are zero. For example, the compounds of formula (I) which correspond to this variant are such that i can also be zero.

According to at least one embodiment, the compound of formula (I) is (3-aminopropyl)triethoxysilane.

Typically the amount of compound of formula (I) can be present in an amount ranging from 0.1% to 50%, such as from 1% to 30% by weight, relative to the weight of the at least one first composition.

According to at least one variant of the disclosure, the at least one first composition is substantially anhydrous. For the purposes of the disclosure, a substantially anhydrous composition has a water content of less than 5% by weight, such as less than 2%, for instance less than 1% by weight, relative to the weight of said composition. It should be noted that the water involved is typically bound water, such as the water of crystallization in salts, or traces of water absorbed by the starting materials used in producing the compositions according to the disclosure.

According to at least another variant of the disclosure, the at least one first composition is aqueous. An aqueous composition for the purposes of the present disclosure means a composition having a water content of greater than or equal to 5% by weight, such as from 5% to 80% by weight, for instance from 10% to 70% by weight, or from 15% to 60% by weight, relative to the weight of said composition.

As indicated above, the at least one first composition comprises at least one fat.

By a fat is meant an organic compound which is insoluble in water at standard temperature (25° C.) and at atmospheric pressure (760 mmHg) (solubility of less than 5% for instance less than 1%, such as less than 0.1%). In addition, these organic compounds can have, for example, lubricating properties. For instance, in the context of the present disclosure, a fat can be a compound selected from a fatty alcohol, a fatty acid, a fatty acid ester, a fatty alcohol ester, a mineral, vegetable, animal or synthetic oil, or a silicone wax. It is recalled that, in the context of the disclosure, fatty alcohols, esters, and acids have at least one saturated or unsaturated, linear or branched hydrocarbon group containing 6 to 30 carbon atoms, which is optionally substituted, for instance by at least one (such as 1 to 4) hydroxyl groups. If they are unsaturated, these compounds may have one to three conjugated or non-conjugated carbon-carbon double bonds.

As oils that may be used in the composition of the disclosure, non-limiting examples include:

hydrocarbon oils of animal origin, such as perhydrosqualene;

hydrocarbon oils of plant origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil, and shea butter oil;

linear or branched hydrocarbons of mineral or synthetic origin, such as liquid paraffins, and derivatives thereof, petrolatum, liquid petrolatum, polydecenes, hydrogenated polyisobutenes such as PARLEAM®; and isoparaffins, for instance isohexadecane and isodecane;

the fatty alcohols are saturated or unsaturated, linear or branched, and contain from 8 to 30 carbon atoms; they include cetyl alcohol, stearyl alcohol and a mixture thereof (cetylstearyl alcohol), octyldodecanol, 2-butyloctanol, 2-hexyldecanol, 2-undecylpentadecanol, oleyl alcohol, or linoleyl alcohol;

fluoro oils with partial hydrocarbon and/or silicone modification, such as those described in document JP-A-2-295912; fluoro oils also include perfluoromethyl-cyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The wax or waxes are selected for example, from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy raw materials that may be used according to the disclosure are marine waxes such as the product sold by the company Sophim under the reference M82, and polyethylene waxes or polyolefin waxes in general.

The fatty acids may be saturated or unsaturated and contain from 6 to 30 carbon atoms, such as from 9 to 30 carbon atoms. For example, they may be selected from myristic acid, palmitic acid, stearic acid, behenic acid, oleic acid, linoleic acid, linolenic acid and isostearic acid.

The esters are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

In at least one embodiment, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may also be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters discussed above, further mention may be made of ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ such as $C_{12}$-$C_{22}$ fatty acids. It is recalled that the term "sugar" means oxygen-bearing hydrocarbon compounds which contain several alcohol functions, with or without aldehyde or ketone functions, and which contain at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose and lactose, and derivatives thereof, including alkyl derivatives, such as methyl derivatives, for instance methylglucose.

The sugar esters of fatty acids may be selected for instance from the group containing the esters or mixtures of esters of sugars described previously and of linear or branched, saturated or unsaturated $C_6$-$C_{30}$, such as $C_{12}$-$C_{22}$ fatty acids. If they are unsaturated, these compounds may comprise one to three conjugated or non-conjugated carbon-carbon double bonds.

The esters according to this variant may also be selected from mono-, di-, tri-, tetraesters and polyesters, and mixtures thereof.

These esters may be selected, for example, from oleates, laurates, palmitates, myristates, behenates, cocoates, stearates, linoleates, linolenates, caprates and arachidonates, or mixtures thereof such as, oleo-palmitate, oleo-stearate and palmitostearate mixed esters.

For example, use can be made of monoesters and diesters such as sucrose, glucose or methylglucose mono- or di-oleates, stearates, behenates, oleo-palmitates, linoleates, linolenates, and oleostearates.

An example that may be mentioned is the product sold under the name GLUCATE® DO by the company Amerchol, which is a methylglucose dioleate.

Further non-limiting examples of esters or mixtures of esters of sugar and of fatty acid include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% di-tri-ester-polyester;

the sucrose mono-dipalmito-stearate sold by the company Goldschmidt under the name TEGOSOFT® PSE.

The silicones that may be used in the cosmetic compositions of the present disclosure are volatile or non-volatile, cyclic, linear or branched silicones, which are unmodified or modified with organic groups, having a viscosity of $5 \times 10^{-6}$ to $2.5$ m$^2$/s at 25° C., for instance, $1 \times 10^{-5}$ to $1$ m$^2$/s.

The silicones that may be used in accordance with the disclosure may be in the form of oils, waxes, resins, or gums.

The silicone can be selected from polydialkylsiloxanes, such as polydimethylsiloxanes (PDMS), and organomodified polysiloxanes comprising at least one functional group selected from poly(oxyalkylene) groups, amino groups, and alkoxy groups.

Organopolysiloxanes are defined in greater detail in Walter Noll's "Chemistry and Technology of Silicones" (1968), Academic Press. They may be volatile or non-volatile.

When they are volatile, the silicones may be selected from those having a boiling point ranging from 60° C. to 260° C., and for instance, from:

(i) cyclic polydialkylsiloxanes containing from 3 to 7, for instance 4 to 5, silicon atoms. These are, for example, octamethylcyclotetrasiloxane sold under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Mention may also be made of cyclocopolymers of the dimethylsiloxane/methylalkylsiloxane type, such as VOLATILE SILICONE® FZ 3109 sold by the company Union Carbide, of formula:

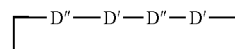

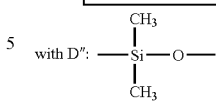

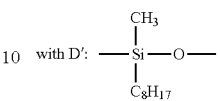

Mention may also be made of mixtures of cyclic polydialkylsiloxanes with organosilicon compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile polydialkylsiloxanes, polydialkylsiloxane gums and resins, polyorganosiloxanes modified with organofunctional groups above, and mixtures thereof, can be used.

These silicones can be chosen from polydialkylsiloxanes, such as polydimethylsiloxanes containing trimethylsilyl end groups. The viscosity of the silicones is measured at 25° C. according to ASTM standard 445 Appendix C.

Among these polydialkylsiloxanes, mention may be made, in a non-limiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60,000 mm$^2$/s;

the VISCASIL® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are polydialkyl($C_1$-$C_{20}$)siloxanes.

The silicone gums that can be used in accordance with the disclosure are polydialkylsiloxanes and polydimethylsiloxanes with high number-average molecular masses ranging from 200,000 to 1,000,000, used alone or as a mixture in a solvent. This solvent can be selected from volatile silicones, polydimethylsiloxane (PDMS) oils, poly-phenylmethylsiloxane (PPMS) oils, isoparaffins, polyisobutylenes, methylene chloride, pentane, dodecane and tridecane, or mixtures thereof.

Products that can be used in accordance with the disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane, mixtures of two PDMSs with different viscosities, for instance a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of 5×10⁻⁶ m²/s. For instance, this product can contain 15% SE 30 gum and 85% SF 96 oil.

The organopolysiloxane resins that can be used in accordance with the disclosure are crosslinked siloxane systems containing the following units:

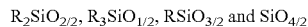

in which R represents an alkyl containing 1 to 16 carbon atoms. For instance, R may denote a $C_1$-$C_4$ lower alkyl group, such as methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of trimethyl siloxysilicate type resins sold under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon group.

Besides the silicones described above, the organomodified silicones may be polydiarylsiloxanes, polydiphenylsiloxanes, and polyalkylarylsiloxanes functionalized with the organofunctional groups mentioned previously.

The polyalkylarylsiloxanes may be selected from linear and/or branched polydimethyl/methylphenylsiloxanes and polydimethyl/diphenylsiloxanes with a viscosity of from $1 \times 10^{-5}$ to $5 \times 10^{-2}$ m²/s at 25° C.

Among these polyalkylarylsiloxanes, examples that may be mentioned include the products sold under the following names:

the SILBIONE® oils of the 70 641 series from Rhodia;
the oils of the RHODORSIL® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$) alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups may be $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

For example, the fat may be a compound that is liquid at a temperature of 25° C. and at atmospheric pressure.

The fat may be a non-silicone fat.

In at least one embodiment, the fat is not selected from fatty acids.

The fat can be selected from liquid petrolatum, liquid paraffin, polydecenes, fatty acid esters, may be liquid, or mixtures thereof, such as, liquid petrolatum, liquid paraffin and fatty acid esters, and mixtures thereof.

The at least one first composition comprising the compound or compounds of formula (I) can have a fat content ranging from 10% to 99% by weight, relative to the weight of the composition; such as ranging from 20% to 90% by weight, for instance ranging from 25% to 80% or ranging from 30% to 70% by weight.

The at least one first composition additionally comprises at least one nonionic surfactant.

The at least one nonionic surfactant may be polyoxyalkylenated, polyglycerolated, or mixtures thereof.

Examples of oxyalkylenated nonionic surfactants include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitan, saturated or unsaturated, oxyethylenated plant oils, condensates of ethylene oxide and/or of propylene oxide, inter alia, alone or as mixtures.

The surfactants contain a number of moles of ethylene oxide and/or of propylene oxide of ranging from 1 to 90, such as ranging from 1 to 50 and ranging from 2 to 30. In at least one embodiment, the nonionic surfactants do not comprise any oxypropylene units.

In accordance with at least one embodiment of the disclosure, the oxyalkylenated nonionic surfactants are selected from oxyethylenated $C_8$-$C_{30}$ alcohols and polyoxyethylenated esters of linear or branched, saturated or unsaturated $C_8$-$C_{30}$ acids, and of sorbitan.

As examples of monoglycerolated or polyglycerolated nonionic surfactants, monoglycerolated or polyglycerolated $C_8$-$C_{40}$ alcohols are used.

The monoglycerolated or polyglycerolated $C_8$-$C_{40}$ alcohols correspond to the following formula:

in which R represents a linear or branched $C_8$-$C_{40}$, such as $C_8$-$C_{30}$ alkyl or alkenyl radical, and m represents a number ranging from 1 to 30, such as from 1 to 10.

As examples of compounds that are suitable in the context of the disclosure, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, two or more species of polyglycerolated fatty alcohol may coexist in the form of a mixture.

Among the monoglycerolated or polyglycerolated alcohols, the $C_8/C_{10}$ alcohol containing 1 mol of glycerol, the $C_{10}/C_{12}$ alcohol containing 1 mol of glycerol and the $C_{12}$ alcohol containing 1.5 mol of glycerol may be used.

The at least one first composition comprises at least one nonionic surfactant selected from polyoxyalkylenated nonionic surfactants, $C_8$-$C_{30}$ alcohols oxyethylenated with 2-3 moles of ethylene oxide, polyoxyethylenated esters of saturated or unsaturated, linear or branched, $C_8$-$C_{30}$ acids and of sorbitan.

The nonionic surfactant content of the at least one first composition ranges from 0.1% to 50% by weight, such as from 0.5% to 30% by weight relative to the weight of this composition.

The at least one first composition comprising the at least one compound of formula (I) may also comprise at least one oxidation dye precursor, such as at least one oxidation base optionally in combination with at least one coupler; at least one synthetic or natural direct dye, or mixtures thereof.

By way of example, the oxidation bases can be selected from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetyl-aminoethyloxy-para-phenylenediamine, N-(β-methoxyethyl)-para-phenylenediamine, 4-aminophenylpyrrolidine, 2-thienyl-para-phenylenediamine, 2β-hydroxyethylamino-5-aminotoluene and 3-hydroxy-1-(4'-aminophenyl)pyrrolidine, and the addition salts thereof with an acid.

The para-phenylenediamines mentioned above may include for instance, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)-amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2

359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-diamino-1-(β-methoxyethyl)pyrazole may also be used.

Pyrazole derivatives that may also be mentioned include diamino-N,N-dihydropyrazolopyrazolones and those described in patent application FR 2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Heterocyclic bases that will typically be used include 4,5-diamino-1-(β-hydroxyethyl)pyrazole and/or 2,3-diamino-6,7-dihydro-1H,5H-pyrazolo[1,2-a]pyrazol-1-one and the addition salts thereof.

The composition according to the disclosure may optionally comprise at least one coupler selected from those conventionally used for the dyeing of keratin fibers.

Among these couplers, mention may be made of meta-phenylenediamines, meta-aminophenols, meta-diphenols, naphthalenic couplers, and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, and 6-methylpyrazolo[1,5-a]benzimidazole, the addition salts thereof with an acid, and mixtures thereof.

In general, the addition salts of the oxidation bases and couplers that may be used in the context of the disclosure may be selected from the addition salts with an acid such as the hydrochlorides, hydrobromides, sulphates, citrates, succinates, tartrates, lactates, tosylates, benzenesulphonates, phosphates, and acetates.

The at least one oxidation base(s), when present in the composition, can be present in an amount ranging from 0.0001% to 10% by weight relative to the weight of the composition, such as from 0.005% to 5% by weight relative to the weight of the composition.

The at least one coupler(s), if present, can be present in an amount ranging from 0.0001% to 10% by weight relative to the total weight of the composition, such as from 0.005% to 5% by weight relative to the weight of the composition.

The composition with the at least one compound of formula (I) may optionally comprise at least one direct dye which may be selected from cationic, neutral, and anionic species.

Examples of suitable synthetic direct dyes that may be mentioned include the following direct dyes: azo dyes; methine dyes; carbonyl dyes; azine dyes; nitro (hetero)aryl dyes; tri(hetero)arylmethane dyes; alone or as mixtures.

The azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family may be compounds comprising at least one sequence selected from >C═C< and —N═C< in which the two atoms are not simultaneously engaged in a ring. However, it is pointed out that one of the nitrogen or carbon atoms of the sequences may be engaged in a ring. For example, the dyes of this family may be derived from compounds of true methine type (comprising at least one abovementioned sequences —C═C—); of azomethine type (comprising at least one sequence —C═N—) with, for example, azacarbocyanines and their isomers, diazacarbocyanines and their isomers, and tetraazacarbocyanines; of mono- and diarylmethane type; of indoamine (or diphenylamine) type; of indophenol type; or of indoaniline type.

As regards the dyes of the carbonyl family, examples include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin dyes.

As regards the dyes of the azine family, mention may be made of azine, xanthene, thioxanthene, fluorindine, acridine, (di)oxazine, (di)thiazine, and pyronin dyes.

The nitro (hetero)aromatic dyes may be nitrobenzene or nitropyridine direct dyes.

As regards the dyes of porphyrin or phthalocyanine type, it is possible to use cationic or non-cationic compounds, optionally comprising at least one metal or metal ion, for instance alkali metals, alkaline-earth metals, zinc, and silicon.

Other examples of suitable synthetic direct dyes that may be mentioned include nitro dyes of the benzene series; azo direct dyes; methine direct dyes; azomethine direct dyes, with diazacarbocyanines and isomers thereof and tetraazacarbocyanines (tetraazapentamethines); quinone direct dyes, such as anthraquinone, naphthoquinone or benzoquinone dyes; azine direct dyes; xanthene direct dyes; triarylmethane direct dyes; indoamine direct dyes; indigoid direct dyes; phthalocyanine and porphyrin direct dyes; alone or in mixtures.

The direct dyes are frequently selected from nitro dyes of the benzene series; azo dyes; azomethine dyes, with the diazacarbocyanines and their isomers, the tetraazacarbocyanines (tetraazapentamethines); anthraquinone direct dyes; triarylmethane direct dyes; alone or in mixtures.

These direct dyes may be selected from nitro dyes of the benzene series; azo direct dyes; azomethine direct dyes, with diazacarbocyanines and their isomers, and tetraazacarbocyanines (tetraazapentamethines); alone or in a mixture.

These dyes may be monochromophoric dyes (i.e. comprising only one dye) or polychromophoric, such as di- or trichromophoric, dyes; the chromophores may be identical or different, and from the same chemical family or otherwise. It should be noted that a polychromophoric dye comprises two or more radicals each derived from a molecule that absorbs in the visible region ranging from 400 to 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

Among the nitrobenzenic direct dyes that may be used according to the disclosure, mention may be made in a non-limiting manner of the following compounds: 1,4-diamino-2-nitrobenzene; 1-amino-2-nitro-4-β-hydroxyethylaminobenzene; 1-amino-2-nitro-4-bis(β-hydroxyethyl)aminobenzene; 1,4-bis(β-hydroxyethylamino)-2-nitrobenzene; 1-β-hydroxyethylamino-2-nitro-4-bis(β-hydroxyethylamino)benzene; 1-β-hydroxyethylamino-2-nitro-4-aminobenzene; 1-β-hydroxyethylamino-2-nitro-4-(ethyl)(β-hydroxyethyl)aminobenzene; 1-amino-3-methyl-4-β-hydroxyethylamino-6-nitrobenzene; 1-amino-2-nitro-4-β-hydroxyethylamino-5-chlorobenzene; 1,2-diamino-4-nitrobenzene; 1-amino-2β-hydroxyethylamino-5-nitrobenzene; 1,2-bis(β-hydroxyethylamino)-4-nitrobenzene; 1-amino-2-tris(hydroxymethyl)methylamino-5-nitrobenzene; 1-hydroxy-2-amino-5-nitrobenzene; 1-hydroxy-2-amino-4-nitrobenzene; 1-hydroxy-3-nitro-4-aminobenzene; 1-hydroxy-2-amino-4,6-dinitrobenzene; 1-β-hydroxyethyloxy-2-β-hydroxyethylamino-5-nitrobenzene; 1-methoxy-2-β-hydroxyethylamino-5-nitrobenzene; 1-β-hydroxyethyloxy-3-methylamino-4-nitrobenzene; 1-β,γ-dihydroxypropyloxy-3-methylamino-4-nitrobenzene; 1-β-hydroxyethylamino-4-β,γ-dihydroxypropyloxy-2-nitrobenzene; 1-β,γ-dihydroxypropylamino-4-trifluoromethyl-2-nitrobenzene; 1-β-hydroxyethylamino-4-trifluoromethyl-2-nitrobenzene; 1-β-hydroxyethylamino-3-methyl-2-nitrobenzene; 1-β-aminoethylamino-5-methoxy-2-nitrobenzene; 1-hydroxy-2-chloro-6-ethylamino-4-nitrobenzene; 1-hydroxy-2-chloro-6-amino-4-nitrobenzene; 1-hydroxy-6-bis(β-hydroxyethyl)amino-3-nitrobenzene; 1-β-hydroxyethylamino-2-nitrobenzene; 1-hydroxy-4-β-hydroxyethylamino-3-nitrobenzene.

Among the monochromophoric azo, azomethine, and methine direct dyes that may be used according to the disclosure, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Non-limiting mention may also be made of the cationic direct dyes chosen from those of formulae (A) and (B):

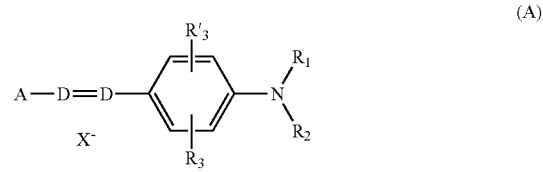

(A)

in which:

D represents a nitrogen atom or the —CH group, $R_1$ and $R_2$, which are identical or different, represent a hydrogen atom; a $C_1$-$C_4$ alkyl radical which may be substituted by a —CN, —OH or —NH$_2$ radical, or form, with a carbon atom of the benzene ring, an optionally oxygen-containing or nitrogen-containing heterocycle which may be substituted by at least one $C_1$-$C_4$ alkyl radical; a 4'-aminophenyl radical, $R_3$ and $R'_3$, which are identical or different, represent a hydrogen or halogen atom selected from chlorine, bromine, iodine and fluorine, or a cyano, $C_1$-$C_4$ alkyl, $C_1$-$C_4$ alkoxy or acetyloxy radical, $X^-$ represents an anion typically selected from chloride, methyl sulphate, and acetate, A represents a group selected from the following structures:

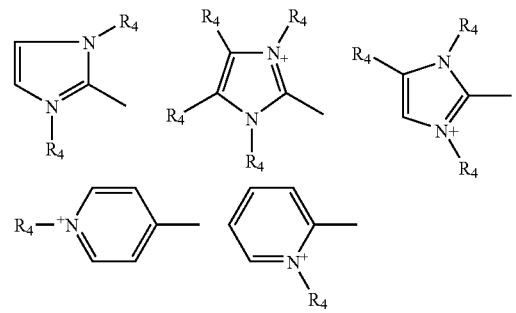

in which $R_4$ represents a $C_1$-$C_4$ alkyl radical which may be substituted by a hydroxyl radical;

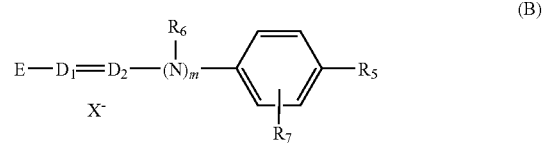

(B)

in which:

$R_5$ represents a hydrogen atom, a $C_1$-$C_4$ alkoxy radical or a halogen atom such as bromine, chlorine, iodine, or fluorine, $R_6$ represents a hydrogen atom or a $C_1$-$C_4$ alkyl radical or forms, with a carbon atom of the benzene ring, a heterocycle which is optionally oxygen-containing and/or substituted by at least one $C_1$-$C_4$ alkyl group, $R_7$ represents a hydrogen or halogen atom such as bromine, chlorine, iodine, or fluorine, $D_1$ and $D_2$, which are identical or different, represent a nitrogen atom or the —CH group, m=0 or 1, $X^-$ represents a cosmetically acceptable anion which may be selected from chloride, methyl sulphate, and acetate, E represents a group selected from the following structures:

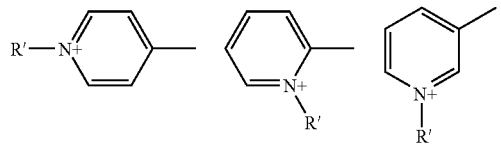

in which R' represents a $C_1$-$C_4$ alkyl radical;

when m=0 and when $D_1$ represents a nitrogen atom, E may then also denote a group of the following structure:

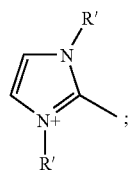

in which R' represents a $C_1$-$C_4$ alkyl radical.

Examples of the aforementioned compounds include the following compounds:

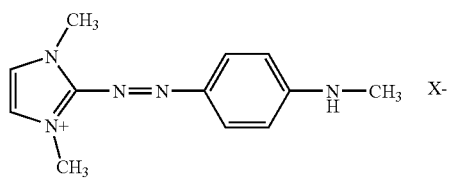
(A1)

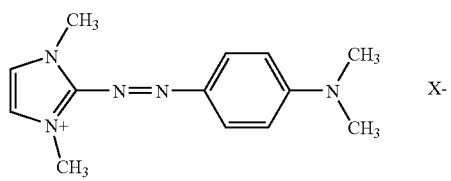
(A2)

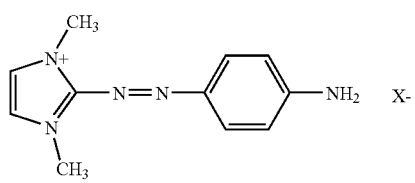
(A3)

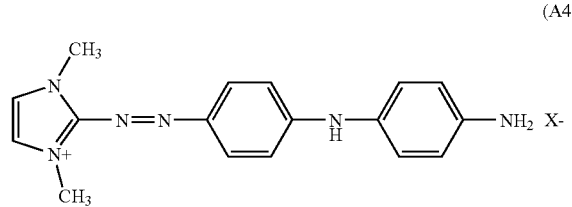
(A4)

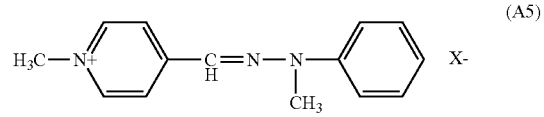
(A5)

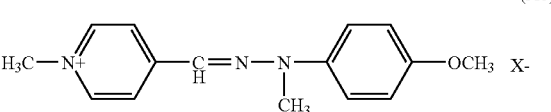
(A6)

The tetraazapentamethine dyes that can be used according to the disclosure include the following compounds appearing in the table below:

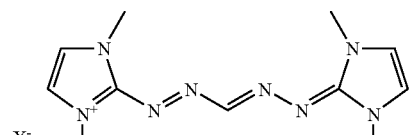

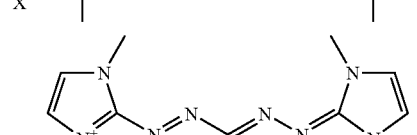

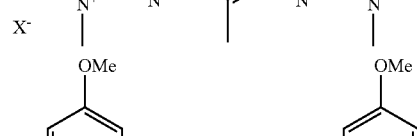

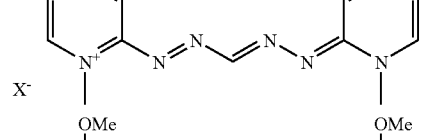

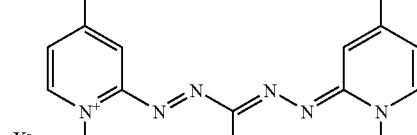

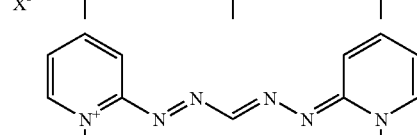

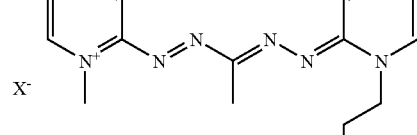

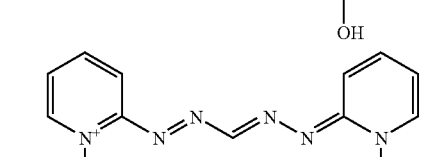

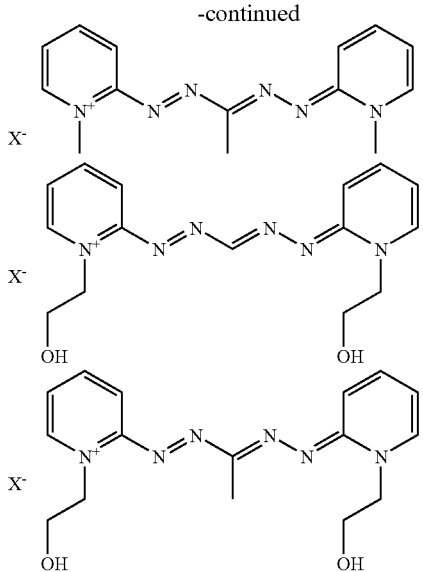

X⁻ represents an anion which may be selected from chloride, iodide, methyl sulphate, ethyl sulphate, and acetate.

Other dyes which may be used according to the disclosure further include, among the azo direct dyes, the following dyes, which are described in the Colour Index International, 3rd edition: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; Solvent Orange 7; 1-(4'-aminodiphenylazo)-2-methyl-4-bis(β-hydroxyethyl) aminobenzene (INCI name: HC Yellow 7).

Among the quinone direct dyes that may be mentioned are the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99. It is also possible to mention the following compounds: 1-N-methylmorpholiniumpropylamino-4-hydroxyanthraquinone; 1-aminopropylamino-4-methylaminoanthraquinone; 1-aminopropylaminoanthraquinone; 5-β-hydroxyethyl-1,4-diaminoanthraquinone; 2-aminoethylaminoanthraquinone; 1,4-bis(βγ-dihydroxypropylamino)anthraquinone, and also the coumarin compound Disperse Yellow 82.

Among the azine dyes that may be mentioned are the following compounds: Basic Blue 17; Basic Red 2; Solvent Orange 15.

Among the triarylmethane dyes that may be used according to the disclosure, mention may be made of the following compounds: Basic Green 1; Basic Violet 3; Basic Violet 14; Basic Blue 7; Basic Blue 26.

Among the indoamine dyes that can be used according to the disclosure, mention may be made of the following compounds: 2-β-hydroxyethylamino-5-[bis(β-4'-hydroxyethyl)amino]anilino-1,4-benzoquinone; 2-β-hydroxyethylamino-5-(2'-methoxy-4'-amino)anilino-1,4-benzoquinone, 3-N(2'-chloro-4'-hydroxy)phenylacetylamino-6-methoxy-1,4-benzoquinone imine; -3-N(3'-chloro-4'-methylamino)phenylureido-6-methyl-1,4-benzoquinone imine; 3-[4'-N-(ethylcarbamylmethyl)amino]phenylureido-6-methyl-1,4-benzoquinone imine.

The cationic direct dyes can be selected from monochromophoric direct dyes of the following types: azo dyes, true methines; azomethines, with diaza-carbocyanines and their isomers, and tetraazacarbocyanines (tetraazapentamethines); anthraquinones; alone or in a mixture.

If they are present, the amount of synthetic direct dye(s) ranges from 0.005% to 20%, such as from 0.01% to 10%, for example from 0.05% to 5%, by weight, relative to the total weight of the composition.

The composition may further comprise at least one natural direct dye, such as lawsone, juglone, alizarin, purpurin, carminic acid, kermesic acid, purpurogallin, isatin, indigo, protocatechaldehyde, anthocyans and anthocyanidines, curcumin, orceins, apigeninidin, hematein, hematoxylin, brasilin, and brasilein. These compounds may be used as such or from extracts.

If they are present, the amount of natural dye(s) ranges from 0.005% to 20%, such as from 0.01% to 10%, for instance from 0.05% to 5%, by weight, relative to the total weight of the composition.

The at least one first composition may optionally comprise at least one alkaline agent.

The alkaline agent or agents may be different than those of formula (I) and may be, for example, selected from organic amines or salts thereof, inorganic bases, ammonium salts, or mixtures thereof. Note that if the at least one first composition is aqueous, the alkaline agent may be aqueous ammonia.

The organic amines employed as alkaline agent may be selected from organic amines whose $pK_b$ at 25° C. is less than 12, such as less than 10, for instance less than 6.

It should be noted that the $pK_b$ in question is the $pK_b$ corresponding to the function of highest basicity.

The organic amine or amines according to the disclosure may not contain a fatty chain comprising more than 10 carbon atoms.

The organic amine may comprise at least one primary, secondary, or tertiary amine function and at least one linear or branched $C_1$-$C_8$ alkyl group which carry at least one hydroxyl radical.

Also suitable for the implementation of the disclosure are organic amines, which may be selected from alkanolamines, such as mono-, di- or tri-alkanolamines, comprising one to three identical or different $C_1$-$C_4$ hydroxyalkyl radicals.

Among the compounds of this type that may be mentioned are monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable are organic amines having the following formula:

in which W is a $C_1$-$C_6$ alkylene residue optionally substituted with a hydroxyl group or a $C_1$-$C_6$ alkyl radical; Rx, Ry, Rz and Rt, which are identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine, and spermidine.

The organic amine may also be selected from amino acids.

The amino acids that may be used are of natural or synthetic origin, in L, D or racemic form, and comprise at least one acid function selected, for instance, from carboxylic acid, sulphonic acid, phosphonic acid and phosphoric acid functions. The amino acids may be in neutral or ionic form.

As amino acids that may be used in the present disclosure, mention may be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

The amino acids are basic amino acids comprising an additional amine function optionally included in a ring or in a ureido function.

Such basic amino acids may be selected from those corresponding to formula (III) below:

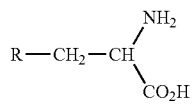
(III)

in which R denotes a group chosen from:

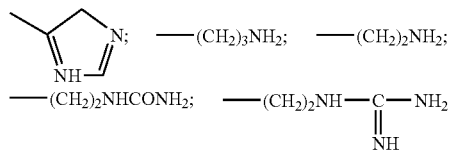

The compounds corresponding to the formula (III) are histidine, lysine, arginine, ornithine, and citrulline.

According to at least one variant of the disclosure, the amino acid is basic and may be selected from arginine, lysine, and histidine, or mixtures thereof.

Alternatively the organic amine may be selected from organic amines of heterocyclic type. Besides histidine, that has already been mentioned in the amino acids, mention may be made of pyridine, piperidine, imidazole, triazole, tetrazole, and benzimidazole.

Additionally the organic amine may be selected from amino acid dipeptides. As amino acid dipeptides that may be used in the present disclosure, mention may be made of carnosine, anserine, and baleine.

Furthermore, the organic amine may be selected from compounds comprising a guanidine function. As amines of this type that may be used in the present disclosure, besides arginine, that has already been mentioned as an amino acid, mention may be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl] amino)ethane-1-sulphonic acid.

Use may also be made of salts of the aforementioned amines, such as the organic and inorganic salts of an organic amine as described below.

For example, the organic salts are selected from the salts of organic acids, such as citrates, lactates, glycolates, gluconates, acetates, propionates, fumarates, oxalates, and tartrates.

For example, the inorganic salts are selected from hydrohalides (for example hydrochlorides), carbonates, hydrogen carbonates, sulphates, hydrogen phosphates and phosphates.

The inorganic base or bases are selected from those possessing in their structure at least one element from columns 1 to 13 of the Periodic Table of the Elements other than hydrogen, not simultaneously comprising carbon and hydrogen atom(s). According to at least one embodiment of the disclosure, the inorganic base contains at least one element from columns 1 and 2 of the Periodic Table of the Elements other than hydrogen.

In at least one embodiment, the inorganic base has the following structure (IV):

$$(Z_1^{x-})_m(Z_2^{y+})_n \quad (IV)$$

in which $Z_2$ denotes a metal from columns 1 to 13, such as from columns 1 or 2 of the Periodic Table of the Elements, for instance sodium or potassium;

$Z_1^{x-}$ denotes an anion chosen from the ions $CO_3^{2-}$, $OH^-$, $HCO_3^{2-}$, $SiO_3^{2-}$, $HPO_4^{2-}$, $PO_4^{3-}$ and $B_4O_7^{2-}$, for instance, chosen from the ions $CO_3^{2-}$, $OH^-$ and $SiO_3^{2-}$;

x denotes 1, 2, or 3;

y denotes 1, 2, 3, or 4;

m and n denote, independently of each other, 1, 2, 3 or 4; with n·y=m·x.

The inorganic base may correspond to the following formula $(Z_1^{x-})_m(Z_2^{y-})_n$, in which $Z_2$ denotes a metal from columns 1 and 2 of the Periodic Table of the Elements; $Z_1^{x-}$ denotes an anion chosen from the ions $CO_3^{2-}$, $OH^-$ and $SiO_3^{2-}$, x is 1, y denotes 1 or 2, and m and n denote, independently of each other, 1 or 2 with n·y=m·x.

As inorganic bases that may be used according to the disclosure, mention may be made of sodium carbonate, potassium carbonate, sodium hydroxide, potassium hydroxide, sodium metasilicate and potassium metasilicate. The inorganic base includes an alkali metal carbonate.

The ammonium salts may be selected from carbonate or bicarbonate salts.

For example, ammonium carbonate may be used.

In at least one embodiment, the at least one first composition may contain no persalts.

The alkaline agent may be selected from alkanolamines, basic amino acids and alkali metal carbonates or hydroxides. For instance, the alkaline agent may be selected from alkanolamines, optionally in a mixture with basic amino acids and/or alkali metal carbonates or hydroxides.

According to at least one embodiment of the disclosure, the alkaline agent is monoethanolamine, which is used alone or in a mixture with the aforementioned alkaline agents, for instance with an inorganic base such as, for example, sodium hydroxide or potassium carbonate, and/or with a basic amino acid such as arginine.

If the at least one first composition comprises at least one alkaline agent, it is present in a content ranging from 0.01% to 30% by weight, such as ranging from 0.1% to 20% by weight, relative to the weight of said composition.

One of the actions of this alkaline agent is to regulate the pH of the composition which is applied to hair, or at any rate its aqueous component, if present. This pH may range from 4 to 11, such as from 7 to 10.5.

If, the at least one first composition is aqueous, aqueous ammonia is employed as alkaline agent, then its amount is less than or equal to 0.03% by weight of the final composition (expressed as $NH_3$), for instance, less than or equal to 0.01% by weight relative to the final composition. It is recalled that the final or "ready to use" composition results from the mixing of the composition comprising the at least one compound of formula (I) with the oxidizing composition, this mixing being carried out either prior to application to the keratin fibers (extemporaneous preparation), or directly to the keratin fibers (separate, successive application, without intermediate rinsing, of the compositions to the keratin fibers). In at least one embodiment, aqueous ammonia is not employed as alkaline agent.

The composition comprising the at least one compound of formula (I) may also contain at least one adjuvant conventionally used in compositions for coloring or decoloring the hair, such as anionic, amphoteric or zwitterionic surfactants, anionic, cationic, nonionic, amphoteric or zwitterionic polymers or mixtures thereof; mineral thickeners, for example fillers such as clays or talc; organic thickeners, such as with anionic, cationic, nonionic and amphoteric polymeric associative thickeners; antioxidants; penetrants; sequestrants; fragrances; dispersants; film-forming agents; ceramides; preservatives; opacifiers, conditioning agents and cationic polymers.

The adjuvants above are generally present in an amount, for each of them, of ranging from 0.01% to 20% by weight relative to the weight of the composition.

In those cases where the at least one first composition is aqueous, it may take the form of a direct emulsion (oil-in-water emulsion). It may be the result of the extemporaneous mixing of the at least one compound of formula (I) with the remainder of said aqueous composition.

When present in the form of a direct emulsion, it may be prepared via conventional processes for preparing direct emulsions, but also via a PIT process.

According to at least one embodiment, the principle of emulsification via the phase inversion temperature (or PIT) is, in its principle, well known to those skilled in the art; it was described in 1968 by K. Shinoda (J. Chem. Soc. Jpn., 1968, 89, 435). It has been shown that this emulsification technique makes it possible to obtain stable fine emulsions (K. Shinoda and H. Saito, J. Colloid Interface Sci., 1969, 30, 258). This technique was applied in cosmetics as early as 1972 by Mitsui et al. ("Application of the phase-inversion-temperature method to the emulsification of cosmetics"; T. Mitsui, Y. Machida and F. Harusawa, American Cosmet. Perfum., 1972, 87, 33).

The principle of this technique is as follows: a mixture of an aqueous phase and an oily phase is prepared and is brought to a temperature above the PIT temperature, the phase inversion temperature of the system, which is the temperature at which the equilibrium between the hydrophilic and lipophilic properties of the emulsifier(s) used is reached; at elevated temperature, i.e. above the phase inversion temperature (>PIT), the emulsion is of water-in-oil type, and, during its cooling, this emulsion inverts at the phase inversion temperature, to become an emulsion of oil-in-water type, doing so by passing previously through a state of microemulsion. This process can make it readily possible to obtain emulsions with a diameter of less than 4 µm.

According to this PIT process, the direct emulsion comprises a direct emulsion (oil-in-water) that comprises at least one fat, including at least one oil, at least one surfactant, at least one of which is a nonionic surfactant having a cloud point, and an amount of water of greater than 5% by weight relative to the total weight of the emulsion. According to at least one embodiment, the nonionic surfactant has an HLB ranging from 8 to 18. Moreover, such an emulsion has a particle size of less than 4 µm, such as less than 1 µm.

In greater detail, it is possible to work as follows to obtain a PIT emulsion:
1) weighing out in a container all the constituents of the direct emulsion,
2) homogenizing the mixture, for example using a Rayneri blender at 350 rpm, while heating by gradually increasing the temperature using a water bath, up to a temperature greater than the phase inversion temperature T1, i.e. until a transparent or translucent phase is obtained (microemulsion zone or lamellar phase), and then until a more viscous phase is obtained, which indicates that the inverse emulsion (W/O) has been obtained,
3) stopping the heating and continuing stirring until the emulsion has cooled to room temperature, passing through the phase inversion temperature T1, i.e. the temperature at which a fine O/W emulsion forms,
4) when the temperature has fallen below the phase inversion temperature region (T1), adding the optional additives and the heat-sensitive starting materials.

A stable final composition in which the droplets of the lipophilic phase are fine, with sizes from 10 to 200 nm, is obtained.

In the zone of formation of a microemulsion (translucent mixture), the hydrophilic and hydrophobic interactions are equilibrated since the surfactant has a tendency to form both direct micelles and inverse micelles. By heating beyond this zone, there is formation of a W/O emulsion since the surfactant favours the formation of a water-in-oil emulsion. Next, on cooling below the phase inversion zone, the emulsion becomes a direct emulsion (O/W).

Emulsification by phase inversion is explained in detail in the publication by T. Förster, W. von Rybinski and A. Wadle, Influence of microemulsion phases on the preparation of fine disperse emulsions, Advances in Colloid and Interface Sciences, 58, 119-149, 1995, which is cited herein for reference.

In the cases where the at least one first composition is substantially anhydrous, it may result from the extemporaneous mixing of the at least one compound of formula (I) with the rest of the ingredients of the at least one first composition.

The coloring method according to the disclosure is implemented by applying to the wet or dry keratin fibers the at least one first composition as defined above, in the presence of at least one aqueous oxidizing composition.

The oxidizing composition is aqueous and it may optionally comprise at least one organic solvent.

Organic solvents include, for example, linear or branched $C_2$-$C_4$ alkanols, such as ethanol and isopropanol; glycerol; glycols and glycol ethers, for instance 2-butoxyethanol, propylene glycol, dipropylene glycol, propylene glycol monomethyl ether, diethylene glycol monoethyl ether and monomethyl ether, and also aromatic alcohols such as benzyl alcohol or phenoxyethanol, and mixtures thereof.

The solvent or solvents may be present in an amount ranging from 1% to 40% by weight relative to the weight of the oxidizing composition, such as ranging from 5% to 30% by weight.

The oxidizing agent may be selected from hydrogen peroxide; urea peroxide; alkali metal ferricyanides or bromides; peroxygenated salts such as, for example, persulphates, perborates and percarbonates of alkali metals or alkaline earth metals, such as sodium, potassium and magnesium; or mixtures thereof.

This oxidizing agent may be composed of hydrogen peroxide, for instance by an aqueous solution whose titre may range from 1 to 40 volumes, for example ranging from 5 to 40 volumes.

The oxidizing composition may also comprise at least one alkalifying agent and/or at least one acidifying agent. The oxidizing composition may comprise at least one acidifying agent.

Acidifying agents include, for example, organic or inorganic acids, such as hydrochloric acid, orthophosphoric acid, sulphuric acid, carboxylic acids such as acetic acid, tartaric acid, citric acid and lactic acid, and sulphonic acids.

The pH of the oxidizing composition may be less than 7, for instance if the oxidizing agent is hydrogen peroxide.

The oxidizing composition may be present in the form of a solution, an emulsion or a gel.

The amount of water in the at least one first composition may range from 5% to 95% by weight, such as ranging from 25% to 92% by weight, for instance ranging from 40% to 90% by weight, relative to the weight of the at least one second composition.

The amount of water in the at least one second composition may range from 10% to 90% by weight, relative to the weight of the emulsion.

When the at least one second composition is an oil-in-water emulsion, it comprises at least one fat as described in the context of the at least one first composition.

The at least one second composition according to the disclosure may comprise at least 10% of fat. The fat concentration ranges from 10% to 80%, such as ranging from 15% to 65% and 20% to 55% of the total weight of the emulsion. According to at least one embodiment, the emulsion comprises at least one oil. Examples include liquid petrolatum, liquid paraffin, polydecenes, and liquid fatty alcohol or fatty acid esters.

The at least one second composition may also comprise at least one surfactant.

The at least one surfactant can be selected from, for example nonionic surfactants or from anionic surfactants.

The at least one surfactant present in the emulsion may be an ethoxylated nonionic surfactant having an HLB ranging from 8 to 18. The HLB is the ratio between the hydrophilic moiety and the lipophilic moiety in their molecule. This term HLB is well known to a person skilled in the art and is described in "The HLB system. A time-saving guide to Emulsifier Selection" (published by ICI Americas Inc.; 1984).

In at least one embodiment, the composition contains no glycerolated surfactants.

The amount of surfactants in the at least one second composition may represent from 0.1% to 50% by weight, such as from 0.5% to 30% by weight, relative to the weight of the emulsion.

According to at least one embodiment, when the at least one second composition is a direct emulsion, it may be prepared by conventional processes for preparing direct emulsions, but also by a PIT process. The oxidizing direct emulsion can be prepared by a PIT process. Reference may be made to the description given above of this type of preparation process, in the context of the preparation of the at least one first composition when the latter is in aqueous form, and it will not be detailed once again in this section.

The oxidizing composition may also contain other ingredients which are conventionally employed in the art, such as those detailed earlier on above in the context of the compositions comprising the at least one compound of formula (I).

According to at least one embodiment of the disclosure, the amount of oxidizing composition relative to the amount of the at least one first composition comprising the compound or compounds of formula (I) is such that the amount of the at least one compound of formula (I) ranges from 2% to 8% by weight in the final composition. It is recalled that the final composition is defined as the composition resulting from the mixing of the composition comprising the compound or compounds of formula (I) with the oxidizing composition, this mixing being carried out either before application to the keratin fibers (extemporaneous preparation) or directly to the keratin fibers (separate, successive application, without intermediate rinsing, of the compositions to the keratin fibers).

According to at least one embodiment of the disclosure, the process is implemented by applying to the wet or dry keratin fibers a composition obtained by extemporaneous mixing, at the time of use, of the composition comprising the compound or compounds of formula (I) (at least one first composition) and the oxidizing composition (at least one second composition).

According to at least one embodiment of the disclosure, the process is implemented by applying the two compositions to the wet or dry keratin fibers successively and without intermediate rinsing.

The process may be implemented for example, by applying to the wet or dry keratin fibers, successively and without intermediate rinsing, such as with water, the composition comprising the compound or compounds of formula (I) (at least one first composition) and then the oxidizing composition (at least one second composition) or else the oxidizing composition and then the at least one first composition.

Irrespective of which variant of the process is employed, the mixture present on the fibers (either resulting from the extemporaneous mixing or else resulting from the successive application of the composition comprising at least one compound of formula (I) and the oxidizing composition) is left in place for a time in general of the order of 1 minute to 1 hour, such as from 10 minutes to 30 minutes.

The temperature during the method may range from the ambient temperature (range of 15 to 25° C.) to 80° C., such as ranging from ambient temperature to 60° C.

At the end of the treatment, the human keratin fibers are optionally rinsed with water, washed with shampoo, rinsed again with water, and then dried or left to dry.

The disclosure also provides a multiple-compartment device comprising in at least one compartment at least one first composition comprising at least one compound of formula (I) as defined above, and in at least another compartment at least one second composition comprising at least one oxidizing agent also described previously.

The examples which follow serve to illustrate the disclosure, though without any limitative character.

EXAMPLES

Example 1

Substantially Anhydrous First Composition

The following compositions are prepared:
Anhydrous composition A (amounts expressed in g %)

| | |
|---|---|
| Propylene carbonate | 0.9 |
| Octyldodecanol | 10.35 |
| Glycol distearate | 7.2 |
| Laureth-2 | 0.9 |
| Polysorbate 21 | 10 |
| Disteardimonium hectorite | 2.7 |
| (3-Aminopropyl)triethoxysilane (*) | 10 |
| Liquid paraffin | qs 100 g |

(*) 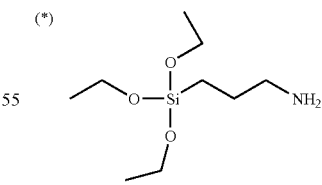

Oxidizing composition B (amounts expressed in g %):

| | |
|---|---|
| Tocopherol | 0.1 |
| Sodium stannate | 0.04 |
| Pentasodium pentetate | 0.06 |
| Polyquaternium-6 | 0.2 |

-continued

| | |
|---|---|
| Glycerol | 0.5 |
| Cetearyl alcohol | 8 |
| Hexadimethrine chloride | 0.15 |
| Ceteareth-33 | 3 |
| Phosphoric acid | qs pH = 3 |
| Hydrogen peroxide | 6 |
| Tetrasodium pyrophosphate | 0.03 |
| Liquid paraffin | 20 |
| Rapeseed acid amide, ethoxylated (4EO), protected | 1.20 |
| Demineralized water | qs 100 g |

At the time of use, 10 g of composition A were mixed with 15 g of composition B.

The resulting mixture (pH=9.7) was applied to a lock of straightened* hair (tone level=4) for 30 minutes at 27° C. on a hot plate.

At the end of this leave-in time, the lock was washed with Elsève multivitamin shampoo, then dried under a hood at 60° C.

Straightening was carried out using the composition Dark and Lovely Super (Softsheen Carson) for 20 minutes at 27° C. on a hot plate. The straightener product/lock ratio was 10/1 (weight/weight) respectively. At the end of the treatment, the hair was rinsed with water, washed with the shampoo Color Signal Neutralizing Shampoo (Dark and Lovely), and then rinsed with water and dried.

Finally, colorimetric reading was carried out on the locks using the Konica Minolta CM2600D colorimeter (10° observer, D65 illuminant).

As shown in the table below, a good level of lightening was obtained.

Moreover, the lock had a soft and smooth feel.

Finally, application was pleasant, with no sharp odor.

| | L* | a* | b* | ΔE*ab |
|---|---|---|---|---|
| Straightened brown hair | 17.35 | 1.58 | 1.36 | / |
| Hair treated with the mixture of the disclosure | 20.25 | 4.9 | 5 | 5.72 |

Example 2

Aqueous First Composition

The following compositions were prepared:
Composition A (preparation by PIT process—the amounts are expressed in g %)

| | |
|---|---|
| Sorbitol | 7 |
| Liquid paraffin | 62.5 |
| Demineralized water | 15 |
| Behenyl alcohol, ethoxylated 10EO | 6 |
| Pure monoethanolamine | 5 |
| (3-Aminopropyl)triethoxysilane (*) | 2.5 |
| Ethyl alcohol, denatured | 2 |

(*) 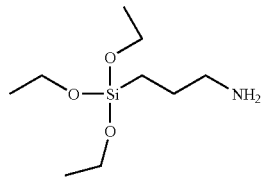

Oxidizing composition B (amounts expressed in g %)

| | |
|---|---|
| Tocopherol | 0.1 |
| Sodium stannate | 0.04 |
| Pentasodium pentetate | 0.06 |
| Polyquaternium-6 | 0.2 |
| Glycerol | 0.5 |
| Cetearyl alcohol | 8 |
| Hexadimethrine chloride | 0.15 |
| Ceteareth-33 | 3 |
| Hydrogen peroxide | 6 |
| Tetrasodium pyrophosphate | 0.03 |
| Liquid paraffin | 20 |
| Rapeseed acid amide, ethoxylated (4EO), protected | 1.20 |
| Phosphoric acid | qs pH = 3 |
| Demineralized water | qs 100 g |

At the time of use, 10 g of composition A were mixed with 15 g of composition B.

The resulting mixture (pH=10) was applied to a lock of straightened* hair (tone level=4) with a bath ratio of 10/1.

Straightening was carried out using the composition Dark and Lovely Super from Softsheen Carson for 20 minutes at 27° C. on a hot plate. The straightener product/lock ratio was 10/1 (weight/weight) respectively.

At the end of the treatment, the hair was rinsed with water, washed with the specific shampoo Color Signal Neutralizing Shampoo (Dark and Lovely), and then rinsed with water and dried.

The leave-in time for the mixture of compositions A and B is 30 minutes at 27° C. on a hot plate.

At the end of this leave-in time, the lock was washed with the shampoo Elsève multivitamines, then dried under a hood at 60° C.

Finally, colorimetric reading was carried out on the locks using the Konica Minolta CM2600D colorimeter (10° observer, D65 illuminant).

As shown in the table below, a good level of lightening was obtained.

Moreover, the lock had a soft and smooth feel.

Finally, application was pleasant, with no sharp odor.

| | L* | a* | b* | ΔE*ab |
|---|---|---|---|---|
| Untreated straightened brown hair | 17.35 | 1.58 | 1.36 | / |
| Hair treated with the mixture of the disclosure | 20.68 | 5.99 | 6.69 | 7.68 |

What is claimed is:
1. A method for coloring and/or lightening human keratin fibers, comprising
applying to the fibers at least one first composition comprising at least one fat, at least one nonionic surfactant, and at least one compound of formula (I):

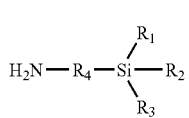

in which:
$R_1$, $R_2$, and $R_3$, which are identical or different, denote:
a linear or branched $C_1$-$C_{20}$ alkoxy radical in which the alkyl moiety is optionally interrupted by at least one oxygen atom,
a linear or branched $C_2$-$C_{20}$ alkenyloxy radical, $R_4$ is a divalent radical of structure:

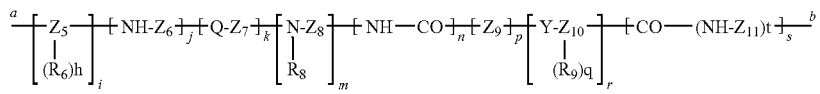

in which:
- $R_6$, identical or different at each occurrence, denotes a linear or branched $C_1$-$C_4$ alkyl radical, which is optionally substituted by at least one entity chosen from hydroxyl groups, $NH_2$ radicals, hydroxyl radicals, cyano radicals, $Z_{12}NH_2$ radicals, $Z_{13}NH$ $Z_{14}NH_2$ radicals, and linear or branched $C_2$-$C_{10}$, alkenyl radicals, with $Z_{12}$, $Z_{13}$ and $Z_{14}$ denoting, independently of one another, a $C_1$-$C_{20}$, linear alkylene radical
- $R_8$ denotes a linear or branched $C_1$-$C_4$ alkyl radical, which is optionally substituted by at least one group chosen from hydroxyl and carboxyl groups, linear or branched $C_2$-$C_{10}$ alkenyl radicals, $Z_{15}NH_2$ radicals, $Z_{16}R_8'$ radicals and $Z_{17}Si\,OSi(R_a)_2(R_b)$ radicals where
- $R_a$ denotes a linear or branched $C_1$-$C_4$ alkoxy radical
- $R_b$ denotes a linear or branched $C_1$-$C_4$ alkyl radical
- $Z_{15}$, $Z_{16}$ and $Z_{17}$ denote, independently of one another, a $C_1$-$C_{20}$ linear alkylene radical
- $R_8'$ denotes a $C_6$-$C_{30}$ aryl radical
- $R_9$ denotes a linear or branched $C_1$-$C_4$ alkyl radical
- $Z_5, Z_6, Z_7, Z_8, Z_9, Z_{10}$ and $Z_{11}$ denote, independently of one another, a $C_1$-$C_{20}$ linear alkylene radical
- Q denotes a ring containing six members which is saturated or unsaturated and optionally comprises at least one heteroatom
- Y, identical or different at each occurrence, represents an oxygen atom, a sulphur atom or an NH group
- h is 0, 1, 2, 3, 4 or 5
- i is 0 or 1
- j is 0, 1, 2 or 3
- k is 0 or 1
- m is 0 or 1
- n is 0 or 1
- p is 0 or 1
- q is 0 or 1
- r is 0, 1, 2 or 3
- s is 0 or 1
- t is 1 or 2
- at least one of the coefficients h, i, j, k, m, n, p, q, r and s is non-zero
- a represents the bond to the silicon atom, and
- b represents the bond to the nitrogen atom of the amino group; and applying to the fibers at least one second, aqueous composition comprising at least one oxidizing agent.

2. The method according to claim 1, wherein $R_1$ and $R_2$ are identical.

3. The method according to claim 1, wherein the compound of formula (I) comprises only one silicon atom.

4. The method according to claim 3, wherein the one silicon atom is bearing three $C_1$-$C_4$ alkoxy groups.

5. The method according to claim 1, wherein $R_1$, $R_2$, and $R_3$ are identical.

6. The method according to claim 1, wherein $R_1$, $R_2$, and $R_3$, which are identical or different, denote a linear or branched $C_2$-$C_4$ alkenyloxy radical.

7. The method according to claim 1, wherein $Z_{12}$, $Z_{13}$, $Z_{14}$, $Z_{15}$, $Z_{16}$, and $Z_{17}$, denote, independently of one another, a $C_1$-$C_4$ linear alkylene radical.

8. The method according to claim 1, wherein k, n, and s are 0.

9. The method according to claim 1, wherein p is 1.

10. The method according to claim 1, wherein the at least one compound of formula (I) is present in an amount ranging from 0.1% to 50% by weight relative to the weight of the at least one first composition.

11. The method according to claim 1, wherein the at least one first composition is substantially anhydrous.

12. The method according to claim 1, wherein the at least one first composition is aqueous.

13. The method according to claim 12, wherein the amount of water in the at least one first composition is greater than or equal to 5% by weight relative to the weight of said composition.

14. The method according to claim 13, wherein the amount of water in the at least one first composition ranges from 5% to 80% by weight relative to the weight of said composition.

15. The method according to claim 1, wherein the at least one first composition further comprises at least one dye substance chosen from oxidation couplers, oxidation bases, and direct dyes.

16. The method according to claim 1, wherein the at least one fat is chosen from: fatty alcohols, fatty acids, fatty acid esters, fatty alcohol esters, mineral oils, vegetable oils, animal oils, synthetic oils, silicones, and waxes.

17. The method according to claim 1, wherein the at least one fat is present in an amount ranging from 10% and 99% by weight, relative to the weight of the composition.

18. The method according to claim 1, wherein the at least one nonionic surfactant is chosen from polyoxyalkylenated compounds, and polyglycerolated compounds.

19. The method according to claim 1, wherein the at least one first composition comprises at least one alkaline agent different from the compounds of formula (I).

20. The method according to claim 1, further comprising mixing the at least one first composition and the at least one second composition before applying the compositions to the keratin fibers.

21. The method according to claim 1, comprising applying the at least one first composition and applying the at least one second composition to the keratin fibers, successively and without intermediate rinsing.

22. A multiple-compartment kit comprising
at least one first compartment containing at least one first composition comprising at least one fat, at least one nonionic surfactant, and at least one compound of formula (I):

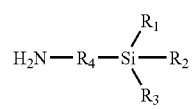

(I)

in which:
$R_1$, $R_2$, and $R_3$, which are identical or different, denote:
a linear or branched $C_1$-$C_{20}$ alkoxy radical in which the alkyl moiety is optionally interrupted by at least one oxygen atom,
a linear or branched $C_2$-$C_{20}$ alkenyloxy radical, $R_4$ is a divalent radical of structure:

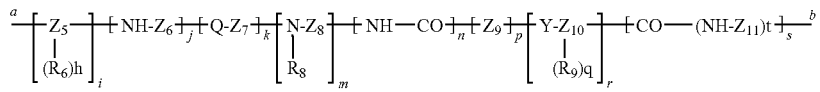

in which:
- $R_6$, identical or different at each occurrence, denotes a linear or branched $C_1$-$C_4$ alkyl radical, which is optionally substituted by at least one entity chosen from hydroxyl groups, $NH_2$ radicals, hydroxyl radicals, cyano radicals, $Z_{12}NH_2$ radicals, $Z_{13}NH\ Z_{14}NH_2$ radicals, and linear or branched $C_2$-$C_{10}$, alkenyl radicals, with $Z_{12}$, $Z_{13}$ and $Z_{14}$ denoting, independently of one another, a $C_1$-$C_{20}$, linear alkylene radical
- $R_8$ denotes a linear or branched $C_1$-$C_4$ alkyl radical, which is optionally substituted by at least one group chosen from hydroxyl and carboxyl groups, linear or branched $C_2$-$C_{10}$ alkenyl radicals, $Z_{15}NH_2$ radicals, $Z_{16}R_8'$ radicals and $Z_{17}Si\ OSi(R_a)_2(R_b)$ radicals where
- $R_a$ denotes a linear or branched $C_1$-$C_4$ alkoxy radical
- $R_b$ denotes a linear or branched $C_1$-$C_4$ alkyl radical
- $Z_{15}$, $Z_{16}$ and $Z_{17}$ denote, independently of one another, a $C_1$-$C_{20}$ linear alkylene radical
- $R_8'$ denotes a $C_6$-$C_{30}$ aryl radical
- $R_9$ denotes a linear or branched $C_1$-$C_4$ alkyl radical
- $Z_5, Z_6, Z_7, Z_8, Z_9, Z_{10}$ and $Z_{11}$ denote, independently of one another, a $C_1$-$C_{20}$ linear alkylene radical
- Q denotes a ring containing six members which is saturated or unsaturated and optionally comprises at least one heteroatom
- Y, identical or different at each occurrence, represents an oxygen atom, a sulphur atom or an NH group
- h is 0, 1, 2, 3, 4 or 5
- i is 0 or 1
- j is 0, 1, 2 or 3
- k is 0 or 1
- m is 0 or 1
- n is 0 or 1
- p is 0 or 1
- q is 0 or 1
- r is 0, 1, 2 or 3
- s is 0 or 1
- t is 1 or 2
- at least one of the coefficients h, i, j, k, m, n, p, q, r and s is non-zero
- a represents the bond to the silicon atom, and
- b represents the bond to the nitrogen atom of the amino group; and
- at least one second compartment containing at least one second composition comprising at least one oxidizing agent.

* * * * *